(12) United States Patent
Shenvi

(10) Patent No.: US 7,064,136 B2
(45) Date of Patent: Jun. 20, 2006

(54) COMPOUNDS

(75) Inventor: Ashokkumar Bhikkappa Shenvi, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 90 days.

(21) Appl. No.: 10/450,284

(22) PCT Filed: Dec. 20, 2001

(86) PCT No.: PCT/SE01/02858

§ 371 (c)(1),
(2), (4) Date: Jun. 11, 2003

(87) PCT Pub. No.: WO02/051807

PCT Pub. Date: Jul. 4, 2002

(65) Prior Publication Data

US 2004/0058916 A1 Mar. 25, 2004

(30) Foreign Application Priority Data

Dec. 22, 2000 (SE) .............................. 0004827

(51) Int. Cl.
*A61K 31/445* (2006.01)
*C07D 417/12* (2006.01)

(52) U.S. Cl. ............. 514/316; 514/211.01; 514/211.08; 514/212.08; 514/218; 514/222.2; 514/222.5; 514/274; 514/316; 514/319; 514/321; 544/129; 544/315; 546/187; 546/188; 546/205; 546/206

(58) Field of Classification Search ............ 514/211.01, 514/211.08, 212.08, 218, 316, 319, 321, 222.2, 514/222.5, 274; 544/129, 315, 332; 546/187, 546/188, 205, 206, 197
See application file for complete search history.

(56) References Cited

U.S. PATENT DOCUMENTS

| 5,521,199 | A | * | 5/1996 | Jacobs et al. ............... 514/331 |
| 5,663,179 | A | | 9/1997 | Dumaitre et al. |
| 5,773,620 | A | * | 6/1998 | Emonds-Alt et al. ....... 546/234 |
| 5,998,444 | A | * | 12/1999 | Russell ...................... 514/331 |
| 6,147,083 | A | * | 11/2000 | Russell ...................... 514/278 |
| 6,365,602 | B1 | * | 4/2002 | Bernstein et al. ........... 514/319 |
| 6,500,818 | B1 | * | 12/2002 | Bernstein et al. ....... 514/211.01 |

FOREIGN PATENT DOCUMENTS

| WO | WO 0002859 A1 | 1/2000 |
| WO | WO 0020003 A1 | 4/2000 |
| WO | WO 0020389 A1 | 4/2000 |
| WO | WO 0069438 | 11/2000 |

OTHER PUBLICATIONS

Baker et al. "Use of NK1 receptor . . . "CA 129:67787 (1998).*

Culman et al, "Effect of Tachykinin Receptor Inhibition in the Brain on Cardiovascular and Behavioral Responses to Stress," The Journal of Pharmacology and Experimental Therapeuics, vol. 280 (No. 1) p. 238–246 (Jun. 9, 1997).

* cited by examiner

*Primary Examiner*—Celia Chang
(74) *Attorney, Agent, or Firm*—Kenneth F. Mitchell

(57) ABSTRACT

A compound having the general formula and methods of using such compounds for the treatment of diseases and pharmaceutical composition comprising such compounds.

10 Claims, No Drawings

COMPOUNDS

RELATED APPLICATIONS

This is the National Stage of PCT Application No. PCT/SE01/02858, filed Dec. 20, 2001, which claims the benefit under 37 C.F.R. § 119(a–d) of Application No. 0004827-2 filed in Sweden on Dec. 22, 2000.

BACKGROUND

The mammalian neurokinins comprise a class of peptide neurotransmitters which are found in the peripheral and central nervous systems. The three principal neurokinins are Substance P (SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists Sp, NKA and NKB, the receptors are classified as neurokinin 1 ($NK_1$), neurokinin 2 ($NK_2$) and neurokinin 3 ($NK_3$) receptors, respectively.

It is now recognized that anxiety, stress, and depression are interrelated conditions (File S E *Pharmacol, Biochem & Behavior* 54/1:3–12, 1996). Moreover, these complex emotional states cannot be due simply to defects in a single neurotransmitter although 5-HT has been ascribed a principal role (Graeff et al., *Pharmacol, Biochem & Behavior* 54/1: 129–141, 1996). Substance P (SP) was one of the first neuropeptides to be identified in mammalian brain and it is now accepted that all three tachykinins are found within the CNS (Iversen L L *J Psychophannacol* 3/1: 1–6, 1989), particularly in the striatonigral neurons, hypothalamus and limbic forebrain (ibid). $NK_1$ and $NK_3$ receptors have been identified in the brain as well (Beaujouan et al., *Neurosci.* 18: 857–875, 1986). Controversy has existed regarding the presence of the $NK_2$ receptor in brain, although recent evidence shows receptor localization in at least the septal region (Steinberg et al., *Eur J Neurosci* 10/7:2337–45 1998).

Pharmacological evidence supporting a role for either $NK_1$ or $NK_2$ receptors in anxiety disorders has been accumulating from assorted animal behavioral tests (for examples, see Table 1). Animal models of depression, however, have been used rarely to define the potential utility of NK receptor antagonists. SP stimulates the turnover of other neurotransmitters involved in depression, i.e., 5-HT in the raphe nucleus, an area thought to be linked to depressive phenomena (Forchetti et al., *J. Neurochem.* 38: 1336–1341, 1982). When injected centrally to nuclei responsible for control of emotion and stress, SP evokes a hemodynamic pressor response bridging this peptide to stress induced hypertension (Ku et al., *Peptides*;19/4:677–82, 1998). Moreover, rises in both heart rate and mean arterial blood pressure evoked by physical stress can be blocked in rodents by centrally administered $NK_1$ receptor antagonists (Culman et al., *J Pharmacol Exp Ther* 280/1:23846, 1997).

TABLE 1

Neurokinin receptor antagonist activity in behavioral tests of anxiety/depression.

| Author | Cpd (Receptor type) | Behavioral Test | Outcome |
|---|---|---|---|
| Teixeira et al., Eur J Pharmacol 5;311(1):7–14, 1996. | $NK_1$ agonists & FK888 ($NK_1$) SR48968 ($NK_2$) | Elevated plus-maze | agonists-anxiogenic antagonists-anxiolytic |
| File Pharm Bio B 58(3):747–752, 1997. | CGP 49823 ($NK_1$) | Social interaction | anxiolytic |
| Vassout et al Neuropeptides 26/S1:38, 1994. | CGP 49823 ($NK_1$) | Social interaction test Elevated plus-maze Forced swim test (depression model) | anxiolytic inactive anti-depressant (only at 30 mg/kb bid) |
| Stratton et al., Eur. J. Pharmacol. 250: R11–12, 1993. | GR100679 ($NK_2$) SR48968 ($NK_2$) | Light-dark box | anxiolytic |
| Walsh et al., Psychopharmacology 121:186–191, 1995. | GR159897 ($NK_2$) SR48968 ($NK_2$) | Light-dark box Marmoset human intruder | anxiolytic anxiolytic |

DESCRIPTION

This invention relates to N-substituted amides; to the manufacture of medicaments containing such compounds; as well as to their uses. These compounds antagonize the pharmacological actions of the neurokinin 1 ($NK_1$) receptor. These compounds are useful whenever such antagonism is desired. Thus, such compounds are of value in the treatment of those diseases in which Substance P is implicated, for example, in the treatment of major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, chronic obstructive pulmonary disorder (COPD), hypertension, migraine, bladder hypermotility, or urticaria.

Accordingly, the present invention provides compounds of the general formula

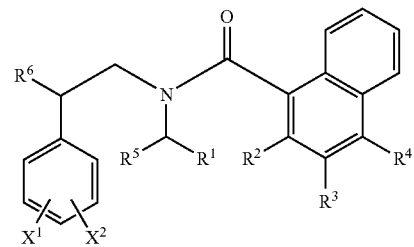

The compounds of the present invention may possess a number of chiral centers, for example at —CH(Ph-$X^1$, $X^2$)—. The present invention covers all isomers, diastereoisomers and mixtures thereof that antagonize $NK_1$.

The preferred configuration at —CH(Ph-$X^1$,$X^2$)— is shown hereinbelow:

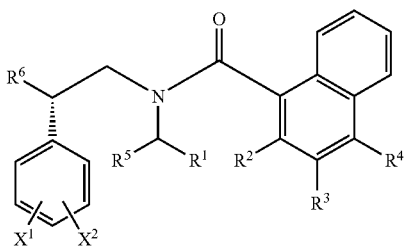

$X^1$ and $X^2$ are independently hydrogen, methyl or halogen. Preferably, $X^1$ and $X^2$ are independently hydrogen or halogen provided that at least one of $X^1$ or $X^2$ is halogen. Most favourably, $X^1$ and $X^2$ are both chloro. In a preferred aspect Ph-$X^1,X^2$ is 3,4-dichlorophenyl.

$R^1$ is $C_{1-4}$alkyl, substituted by 1 or 2 substituents selected from —$NR^aR^a$, —$NR^aC(=O)R^a$, —$C(=O)NR^aR^a$, —$OR^a$, —$OC(=O)R^a$, —$C(=O)OR^a$, —$S(=O)_nC_{1-6}$alkyl, nitro, cyano and $C_{1-3}$haoalolkyl; phenyl substituted by 0, 1, 2 or 3 substituents selected from —$NR^aR^a$, —$NR^aC(=O)R^a$, —$C(=O)NR^aR^a$, —$OR^a$, —$OC(=O)R^a$, —$C(=O)OR^a$, —$S(=O)_nC_{1-6}$alkyl, nitro, cyano and $C_{1-3}$haloallyl; or a 5- or 6-membered ring heterocycle containing 1, 2 or 3 heteroatoms each independently selected from O, N and S and additionally having 0 or 1 oxo groups and 0 or 1 fused benzo rings.

$R^2$ is H, halogen, —$OR^9$ or $C_{1-4}$alkyl.

$R^3$ is H, halogen, —$OR^9$ or —CN.

$R^4$ is H, halogen, —$OR^9$ or $C_{1-4}$alkyl.

$R^5$ is H or $CH_3$.

$R^6$ is halogen, —$CH_2CO_2R^a$, —$CH_2C(=O)H$, —$CH_2CH=CH_2$, —$CH_2CH_2OR^a$, —$CH_2CH_2NR^aR^a$ or

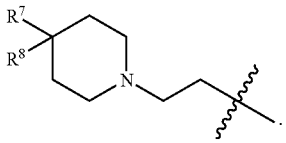

$R^7$ is phenyl substituted by 0, 1, 2 or 3 substituents selected from $C_{1-6}$alkyl, —$NR^aR^a$, —$NR^aC(=O)R^a$, —$C(=O)NR^aR^a$, —$OR^a$, —$OC(=O)R^a$, —$C(=O)R^a$, —$C(=O)OR^a$, —$S(=O)_nC_{1-6}$alkyl, nitro, cyano, $C_{1-3}$haloalkyl, trifluoromethylthio, trifluoromethylsulfmyl, $C_{1-6}$alkanesulfonamido, succinamido, carbamoyl, $C_{1-6}$alkylcarbamoyl, di-$C_{1-6}$alkylcarbamoyl, $C_{1-6}$alkoxy-$C_{1-6}$alkylcarbamoyl, ureido, $C_{1-6}$alkylureido, di($C_{1-6}$alkyl) ureido, bromo, fluoro, chloro and dimethylcarbamoylmethylureido; or $R^7$ is a 5- or 6-membered ring heterocycle containing 1, 2 or 3 heteroatoms each independently selected from O, N and S and additionally having 0 or 1 oxo groups substituted by 0 or 1 substituents selected from —$OR^a$, —$OC(=O)R^a$, —$C(=O)OR^a$, $C(=O)R^a$, —$NR^aR^a$, —$NR^aC(=O)R^a$ and —$C(=O)NR^aR^a$; or $R^7$ is hydrogen or $NR^aR^a$.

$R^8$ is selected from hydrogen, —$OR^a$, —$OC(=O)R^a$, —$C(=O)OR^a$, —$C(=O)R^a$, —$NR^aR^a$, —$NR^aC(=O)R^a$, —$C(=O)NR^aR^a$, $C_{1-6}$alkyl, carbamoyl, $C_{1-6}$alkylcarbamoyl, and bis($C_{1-6}$alkyl)carbamoyl.

$R^a$ is independently at each instance hydrogen or $C_{1-6}$alkyl.

$R^9$ is $C_{1-6}$alkyl, phenyl or phenyl$C_{1-6}$alkyl.

n is 0, 1 or 2.

In one embodiment of the above compounds, $R^1$ is $C_{1-4}$alkyl, substituted by 1 or 2 substituents selected from —$C(=O)NR^aR^a$, —$C(=O)OR^a$ and $C_{1-3}$haloakyl; phenyl substituted by 0, 1, 2 or 3 substituents selected from —$NR^aR^a$, —$NR^aC(=O)R^a$, —$OR^a$, —$OC(=O)R^a$, nitro, cyano and $C_{1-3}$haloalkyl; or a 5- or 6-membered ring heterocycle containing 1, 2 or 3 nitrogen atoms.

In another embodiment of the above compounds, $R^6$ is

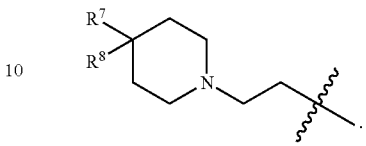

In another embodiment of the above compounds, $R^1$ is $C_{1-4}$alkyl, substituted by 1 or 2 substituents selected from —$C(=O)NR^aR^a$, —$C(=O)OR^a$ and $C_{1-3}$haloalkyl; phenyl substituted by 0, 1, 2 or 3 substituents selected from —$NR^aR^a$, —$NR^aC(=O)R^a$, —$OR^a$, —$OC(=O)R^a$, nitro, cyano and $C_{1-3}$haloalkyl; or a 5- or 6-membered ring heterocycle containing 1, 2 or 3 nitrogen atoms; and $R^6$ is

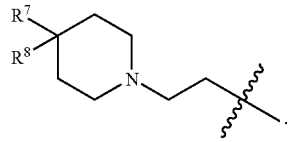

In another embodiment of the above compounds, $R^7$ is phenyl substituted by 0, 1, 2 or 3 substituents selected from $C_{1-6}$alkyl, —$NR^aR^a$, —$NR^aC(=O)R^a$, —$C(=O)NR^aR^a$, —$OR^a$, —$OC(=O)R^a$, —$C(=O)R^a$, —$C(=O)OR^a$, —$S(=O)_nC_{1-6}$alkyl, nitro, cyano, $C_{1-3}$haloalkyl, bromo, fluoro and chloro.

In another embodiment of the above compounds, $R^7$ is a 5- or 6-membered ring heterocycle containing 1 or 2 heteroatoms each independently selected from O, N and S and additionally having 0 or 1 oxo groups substituted by 0 or 1 —$C(=O)NR^aR^a$.

In another embodiment of the above compounds, $R^7$ is $NR^aR^a$.

In another embodiment of the above compounds, $R^8$ is selected from hydrogen, —$NR^aR^a$, —$NR^aC(=O)R^a$ and —$C(=O)NR^aR^a$.

Another aspect of the invention involve a method for manufacturing a medicament comprising an effective amount of an NK1 antagonist according to any of the compounds described above for the treatment of major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypernotility, Huntington's disease, COPD, hypertension, migraine, bladder hypermotility or urticaria.

Another aspect of the invention involves a method of treating major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, COPD, hypertension, migraine, bladder hypermotility, or urticaria comprising administering an effective amount of an $NK_1$ antagonist according to any of the compounds described above.

Particular compounds of this invention are provided as the Examples hereinbelow.

$C_{Y-Z}$alkyl, unless otherwise specified, means an ailyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "$C_{4-7}$alkyl":

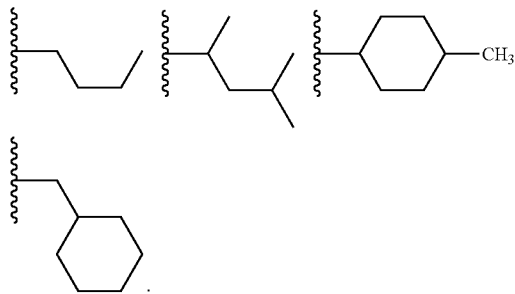

$C_{Y-Z}$haloalkyl, unless otherwise specified, means an alkyl group, as decribed above, wherein any number of the hydrogen atoms usually present on the alkyl are replaced with halogen atoms.

Pharmaceutically-acceptable salts may be prepared from the corresponding acid in conventional manner. Non-pharmaceutically-acceptable salts may be useful as intermediates and as such are another aspect of the present invention.

The term "oxo" means a double bonded oxygen (=O).

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethyl-sulfonate, heptanoate, hexanioate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; diallyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal adminstration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-adninistered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the $NK_1$ receptor is beneficial which comprises administering to a warm-blooded animal an effective amount of a compound of the formula (I) or a pharmaceutically-accepiable salt thereof. The present invention also provides the use of a compound of the formula (I) or a pharmaceutically acceptable salt thereof in the preparation of a medicament for use in a disease condition wherein antagonism of the $NK_1$ receptor is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

It is well known in the art how to prepare optically-active forms (for example, by resolution of the racemic form or by synthesis from optically-active starting materials) and how to determine the $NK_1$ antagonist properties by the standard tests known in the art and those described hereinafter.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

In general, compounds bearing a 2-substituted naphthamide can exist as a mixture of conformational isomers (atropisomers); this is believed to result from slow rotation about the naphthalene amide and/or aryl bonds ("The Chemistry of Rotational Isomers"; Oki, M.; Springer Verlag, N.Y.; 1993). Where individual atropisomers have been isolatable, distinct chemical and biological properties have been observed. The compounds of this invention comprise both mixtures of, and individual, atropisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

SP Receptor Binding Assay (Test A)

The ability of a compound of the invention to antagonize the binding of SP at the $NK_1$ receptor may be demonstrated using an assay using the human $NK_1$ receptor expressed in Mouse Erythroleukemia (MEL) cells. The human $NK_1$ receptor was isolated and characterized as described in: B. Hopkins, et al. "Isolation and characterization of the human lung $NK_1$ receptor cDNA" *Biochem. Biophys. Res. Comm.*, 1991, 180, 1110–1117; and the $NK_1$ receptor was expressed in Mouse Erythroleukemia (MEL) cells using a procedure similar to that described in Test B below.

Neurokinin A (NKA) Receptor Binding Assay (Test B)

The ability of a compound of the invention to antagonize the binding of NKA at the $NK_2$ receptor may be demonstrated using an assay using the human $NK_2$ receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19.

The selectivity of a compound for binding at the $NK_1$ and the $NK_2$ receptors may be shown by determining its binding at other receptors using standard assays, for example, one using a tritiated derivative of NKB in a tissue preparation selective for $NK_3$ receptors. In general, the compounds of the invention which were tested demonstrated statistically significant binding activity in Test A and Test B with a $K_i$ of 1 mM or much less typically being measured.

Rabbit Pulmonary Artery: $NK_1$ in Vitro Functional Assay (Test C)

The ability of a compound of the invention to antagonize the action of the agonist Ac-[$Arg^6$, $Sar^9$, $Met(O_2)^{11}$] Substance P (6–11), ASMSP, in a pulmonary tissue may be demonstrated as follows.

Male New Zealand white rabbits are euthanized via i.v. injection into the ear vein with 60 mg/kg Nembutal (50 mg/mL). Preceding the Nembutal into the vein is Heparin (1000 units/mL) at 0.0025 ml/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); and dl-Propranolol, 0.001 (to block β receptors); gassed continuously with 95% $O_2$-5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1 \times 10^{-6}$ M Thiorphan (to block E.C.3.4.24.11), $3 \times 10^{-8}$ M (S)—N-[2-(3,4-dichlorophenyl)-4-[4-(2-oxoperhydropyrimidin-1-yl)piperidino]butyl]-N-methylbenzamide (to block $NK_2$ receptors), and the given concentration of the compound being tested. At the end of the 1.0 h equilibration, $3 \times 10^{-6}$ M Phenylephrine hydrochloride is added for 1.0 h. At the end of 1.0 h, a dose relaxation curve to ASMSP is done. Each tissue is treated as a individual and is considered finished when it fails to relax fer for 2 consecutive doses. When a tissue is complete, $1 \times 10^{-3}$ M Papaverine is added for maximum relaxation.

Percent inhibition is determined when a tested compound produces a statistically significant (p<0.05) reduction of the total relaxation which is calculated using the total relaxation of the Papaverine as 100%. Potencies of the compounds are determined by calculating the apparent dissociation constants ($K_B$) for each concentration tested using the standard equation:

$$KB = [\text{antagonist}]/(\text{dose ratio} - 1)$$

where dose ratio=antilog[(agonist −log molar $EC_{50}$ without compound)−(−log molar $EC_{50}$ with compound)]. The $K_B$ values may be converted to the negative logarithms and expressed as −log molar KB (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as −log molar $EC_{50}$.

$NK_2$ in Vitro Functional Assay (Test D)

The ability of a compound of the invention to antagonize the action of the agonist [β-ala8] NKA (4–10), BANK, in a pulnonary tissue may be demonstrated as follows. Male New Zealand white rabbits are euthanized via i.v. injection into the ear vein with 60 mg/kg Nembutal (50 mg/mL). Preceding the Nembutal into the vein is Heparin (1000 units/mL) at 0.0025 ml/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose; 11.0; and indomethacin, 0.005 (to inhibit cyclooxygenase); gassed continuously with 95% $O_2$-5% $CO_2$. Responses are measured on a Grass polygraph via Grass FT-03 transducers.

Initial tension placed on each tissue is 2 g, which is maintained throughout the 45 min equilibration period. Tissues are washed with the physiological salt solution at 15 min intervals. After the 45 min equilibration period, $3\times10^{-2}$ M KCl is given for 60 min to test the viability of the tissues. The tissues are then washed extensively for 30 min. The concentration of the compound being tested is then added for 30 min. At the end of the 30 min, a cumulative dose response curve to BANK is performed. Each tissue is treated as a individual and is considered finished when it fails to contract further for 2 consecutive doses. When a tissue is complete, $3\times10^{-2}$ M $BaCl_2$ is added for maximum contraction.

Percent inhibition is determined when a tested compound produces a statistically significant (p<0.05) reduction of the total contraction which is calculated using the total contraction of the $BaCl_2$ as 100%. Potencies of the compounds are determined by calculating the apparent dissociation constants ($K_B$) for each concentration tested using the standard equation:

$$K_B=[\text{antagonist}]/(\text{dose ratio} -1)$$

where dose ratio=antilog[(agonist –log molar $EC_{50}$ without compound)–(–log molar $EC_{50}$ with compound)]. The $K_B$ values may be converted to the negative logarithms and expressed as –log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_1$ and $NK_2$ in Vivo Functional Assay (Test E)

The activity of a compound as an antagonist of $NK_1$ and/or $NK_2$ receptors also may be demonstrated in vivo in laboratory animals as described in: Buckner et al. "Differential Blockade by Tachykinin $NK_1$ and $NK_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.*, 1993, Vol 267(3), pp. 1168–1175. The assay is carried out as follows.

Compounds are tested in anesthetized guinea pigs pretreated with i.v. indomethacin (10 mg/kg, 20 min), propranolol (0.5 mg/kg, 15 min), and thiorphan (10 mg/kg, 10 min).

Antagonists or vehicle are administered i.v. and orally, 30 and 120 min prior to increasing concentrations of agonist, respectively. The agonists used in these studies are ASMSP (Ac-[$Arg^6$,$Sar^9$,$Met(O_2)^{11}$]-SP(6–11)) and BANK (β-ala-8 NKA4–10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm (–log $ED_{50}$). The $ED_{50}$ values, obtained in the presence (P) and absence (A) of antagonist, are used to calculate a Dose Ratio (P/A), an expression of potency. Data are expressed as mean±SEM and statistical differences were determined using ANOVA/Tukey-Kramer and Student's t-test, with p<0.05 considered statistically significant.

Compounds of the present invention exhibit marked activity in the foregoing tests and are considered useful for the treatment of those diseases in which the $NK_1$ and/or $NK_2$ receptor is implicated, for example, in the treatment of asthma and related conditions.

EXAMPLES

The invention will now be illustrated by the following non-limiting examples, in which, unless stated otherwise:

(i) temperatures are given in degrees Celsius (° C.); unless otherwise stated, operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 Pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only, (v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) solvent ratios are given in volume:volume (v/v) terms; and (x) Mass spectra (MS) were run using an automate& system with atmospheric pressure chemical ionization (APCI). Generally, only spectra where parent masses are observed are reported. The lowest mass major ion is reported for molecules where isotope splitting results in multiple mass spectral peaks (for example when chlorine is present).

Terms and abbreviations: solvent mixture compositions are given as volume percentages or volume ratios. In cases where the NMR spectra are complex, only diagnostic signals are reported. atm=atmospheric pressure, Boc=t-butoxycarbonyl, Cbz=benzyloxy-carbonyl, DCM=methylene chloride, DIPEA=diisopropylethylamine, DMF=N,N-dimethylformamide, DMSO=dimethyl sulfoxide, Et$_2$O=diethyl ether, EtOAc=ethyl acetate, equiv.=equivalent(s), h=hour(s), HPLC=high performance liquid chromatography, min=minutes, NMR=nuclear magnetic resonance, psi=pounds per square inch, TFA=tri-fluoroacetic acid, THF=tetrahydrofuran.

Standard reductive amination refers to the typical procedure in which a solution of an amine (1–1.2 equiv.), an aldehyde (1–1.2 equiv.) and acetic acid (2 equiv.) is stirred in methanol for 5 to 60 min before adding NaBH$_3$CN (1.7 equiv.). After 1–16 h the reaction is optionally concentrated, dissolved in DCM, and washed with saturated sodium bicarbonate and then purified by chromatography.

Standard Swern oxidation conditions refer to the oxidation of an alcohol to the corresponding aldehyde according to Mancuso, A J; Huang, S L; Swern, D; J. Org. Chem.; 1978, 2840.

Standard formation of an acid chloride refers to the typical procedure in which a solution of a substituted carboxylic acid in DCM is stirred with 1–1.2 equiv. of oxalyl chloride and a catalytic amount of DMF for 1–12 h, concentrated under reduced pressure, and used without purification.

Standard acylation refers to the typical procedure in which an acid chloride (1–1.2 equiv.) is added to a stirred solution of an amine (1–1.2 equiv.) and triethylariine (2 equiv.) in DCM. After 1–16 h the reaction is optionally concentrated, dissolved in DCM, and washed with saturated sodium bicarbonate and then purified by chromatography.

Where noted that a final compound was converted to the citrate salt, the free base was combined with citric acid (1.0 equiv.) in methanol, concentrated under reduced pressure and dried under vacuum (25–70° C.). When indicated that a compound was isolated by filtration from Et$_2$O, the citrate salt of the compound was stirred in Et$_2$O for 12–18 h, removed by filtration, washed with Et$_2$O, and dried under vacuum at 25–70° C.

Where noted that a final compound was converted to the hydrochloride salt, a solution of HCl in Et$_2$O was added with stirring to a solution of the purified free base in DCM or methanol. The resulting precipitate was collected by filtration and dried under vacuum.

Each compound bearing a 2-substituted naphthamide existed as a mixture of conformational isomers (atropisomers); this is believed to result from slow rotation about the amide and/or aryl bonds. Such compounds generally showed multiple peaks in HPLC chromatograms and highly complex NMR spectra. In some cases, the individual components of an atropisomeric mixture could be purified by reverse phase HPLC and the properties could be independently evaluated.

Analytical HPLC conditions employed were the following: Hewlett Packard HP1100 system using a Luna C18(2) 4.6×75 mm, 3 micron column (Phenomenex; Torrance, Calif.) with the following gradient: 0–0.5 min; 20% Solvent B, then ramping linearly to 85% Solvent B at 15 min at a fixed flow rate of 2 mumin (Solvent A: 0.1% TFA in water; Solvent B: 0.1% TFA in methanol) using UV detection at 255 nm.

Definition of Standard Procedures:

Method A: Standard reductive amination refers to the typical procedure in which a solution of an amine (1–1.2 equivalents), an aldehyde (1–1.2 equivalents) and acetic acid (2 equivalents) are stirred in methanol for 5 to 60 minutes before adding NaBH$_3$CN (1.7 equivalents). After 1–16 h the reaction is optionally concentrated, dissolved in DCM, and washed with saturated sodium bicarbonate and then purified by chromatography.

Method B: Standard acylation refers to the typical procedure in which an acid chloride (1–1.2 equivalents) is added to a stirred solution of an amine (1–1.2 equivalents) and triethylamine (2 equivalents) in DCM. After 1–16 h the reaction is optionally concentrated, dissolved in DCM, and washed with saturated sodium bicarbonate and then purified by chromatography.

Method C: Swern oxidation refers to the typical procedure in which an alcohol is oxidized to the corresponding aldehyde using a literature procedure.

Method D: Where indicated that a compound was isolated as the citrate salt, the free base was combined with citric acid (1.0 equivalents) in methanol, concentrated under reduced pressure and dried under vacuum (25–70° C.). Where indicated that a compound was isolated as the hydrochloride salt, a solution of HCl in Et$_2$O was added with stirring to a solution of the purified free base in DCM or methanol. The resulting precipitate was collected by filtration and dried under vacuum.

Method E: Standard trans amidation reaction in which a methanol solution of the starting material containing ammonia in a sealed tube is heated to 100 C. for 16 h. Upon concentration under reduced pressure the product is purified by chromatography and converted to citrate salt as described in Method D.

Example 1

Method A

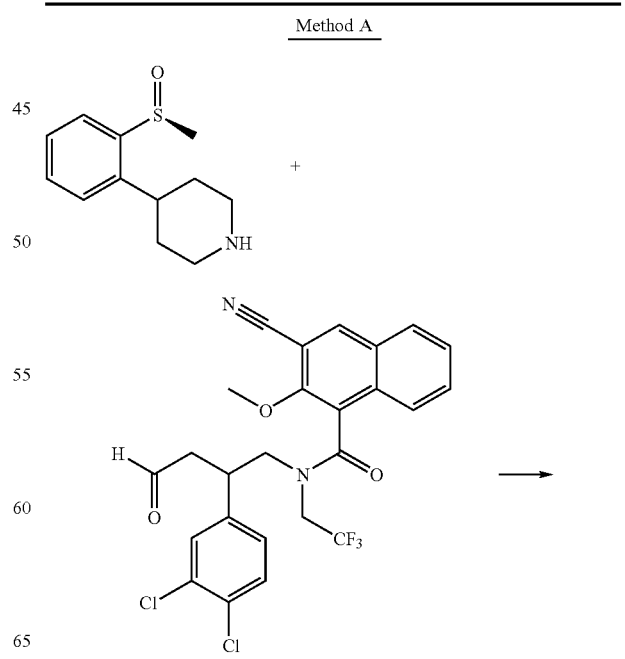

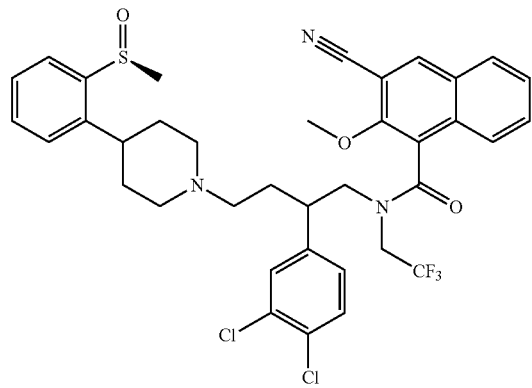
| Salt form | citrate |
|---|---|
| Melting point | 150–160° C. |
| NMR | 8.85(m, 1H), 8.2–6.7(m, 12H), 4.8(br., 1H), 4.4(br., 1H), 3.9(m, 3H), 1.8(br., 5H), |
| Mass Spec | 730 (M + 1) |
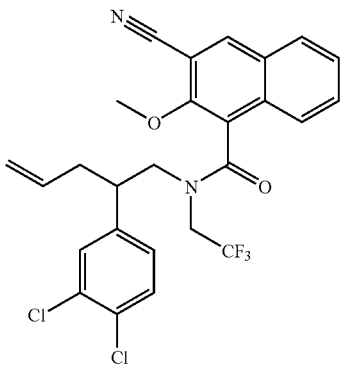
This olefin was prepared from the corresponding amine using procedures B
| NMR | 8.3(m, 1H), 7.9–6.6(m, 7H), 5.2(m, 1H), 4.7(m, 2H), 4.1(m, 3H). |
|---|---|
| Mass Spec | 521 (M + 1) |
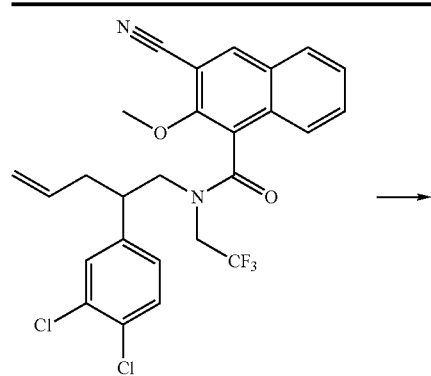
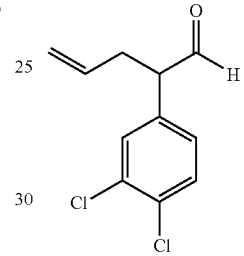 + 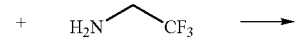 →
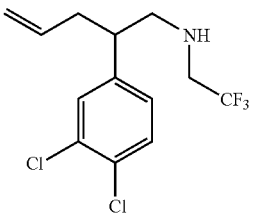
This amine was prepared from the corresponding aldehyde using method A.
| NMR | 7.4(d, J = 4Hz, 1H), 7.25(m, 1H), 7.0(d, d, J1=2Hz, J2=4Hz, 1H), 5.6(m, 1H0, 5.0(m, 2H), 3.0(m, 5H), 2.4 (m, 2H). |
|---|---|
| Mass Spec | 312 (M + 1) |
| NMR | 9.5(three peaks,1H), 8.3(m, 1H), 7.8(m, 2H), 7.5(m, 4H), 7.2(m, 1H), 7.0(m, 1H), 6.9(m, 1H), 6.6(d, d, J1, 2Hz, J2=4Hz), 4,1(m, 3H). |
|---|---|
| Mass Spec | 507 (M − 16) |
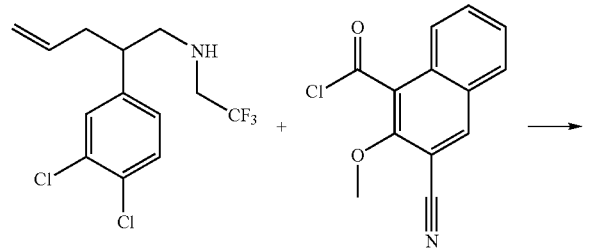
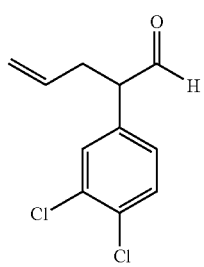

-continued

This aldehyde was prepared from the corresponding alcohol using method C.
NMR     9.7(s, 1H), 7.25(m, 1H), 7.6–7.0(m, 3H), 5.7(m ,1H), 5.0(m, 2H), 3.6(m, 1H).
Mass Spec     229 (M + 1)

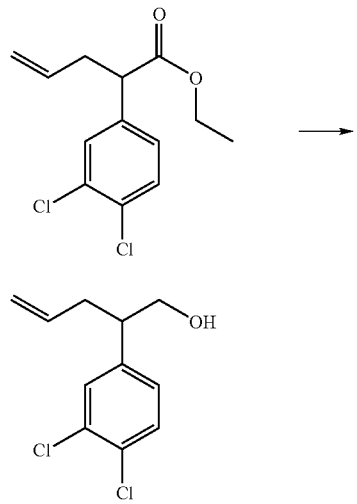

This alcohol was prepared from the corresponding ester using standard lithiumaluminumhydride conditions.
NMR     7.4(d, J=4Hz, 1H), 7.35(d, J=1Hz, 1H), 7.05(d, d, J1= 1Hz, J2=4Hz, 1H), 5.6(m, 1H), 5.0(m, 2H), 3.8(m, 2H), 2.8(m, 1H), 2.4(m, 2H).

Example 2

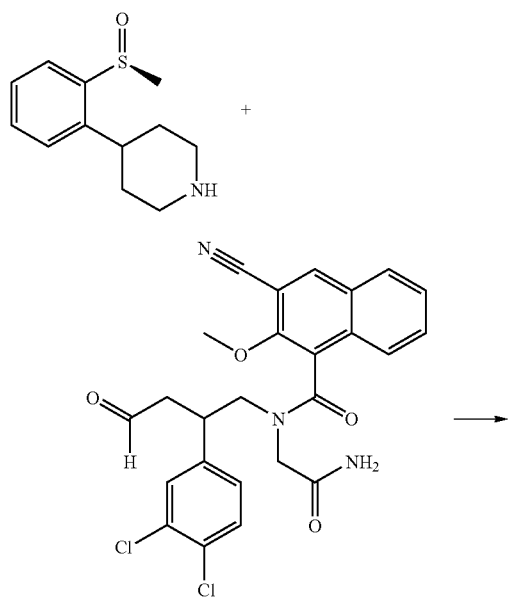

-continued

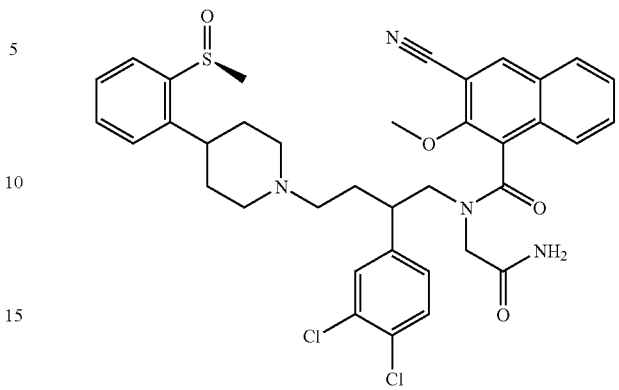

Method A

Salt form     citrate salt
Melting point     185–190° C.
NMR     8.7(m, 1H), 8.3–6.8(m, 12H), 4.0 (m, 3H), 1.6(br., 4H).
Mass Spec     705 (M + 1)

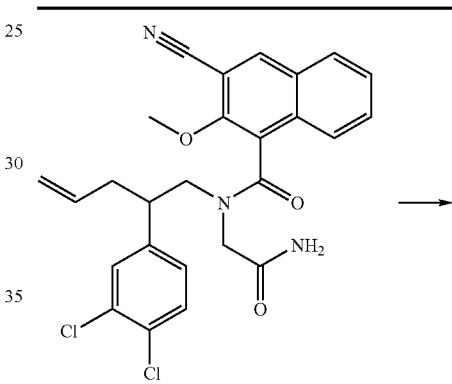

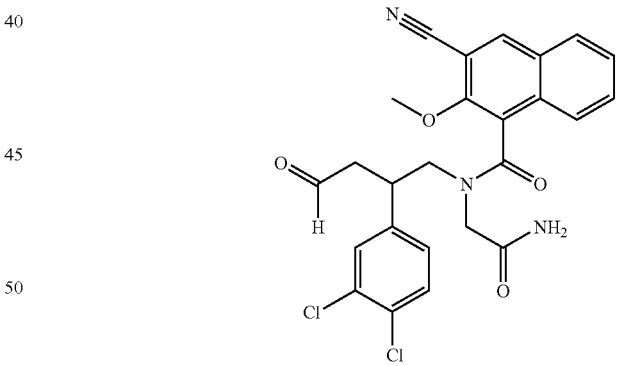

NMR     9.6(three peaks, 1H), 8.3(M, 1H), 8.0–6.6(m, 7H), 4.2 (m, 3H), 2.6(M, 1H).
Mass Spec     498 (M + 1)

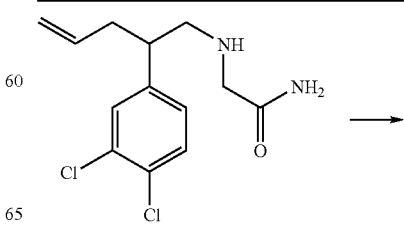

-continued

Method B

| | |
|---|---|
| NMR | 8.3(three peaks, 1H), 8.0–6.2(m, 9H), 4.1 (m, 3H), 2.0(M, 1H). |
| Mass Spec | 496 (M + 1) |

Method A

| | |
|---|---|
| NMR | 7.4(d, 4Hz, 1H), 7.3(d, J=1Hz, 1H), 7.0(d, d, J=1 Hz, J2=4 Hz, 1), 6.8(br., 1H)5.6(m, 1H), 5.0(m, 2H), 3.2(d, J=1Hz, 2H), 2.8(m, 3H), 2.4(m, 2H). |

Example 3

Method A

| | |
|---|---|
| Salt form | citrate |
| NMR | 8.7 (m, 1H), 8.3–6.8(m, 10H), 4.0(two p[eaks, 3H), 3.8 (s, 3H), 1.7(br., 4H). |
| Mass Spec | 735 (M + 1) |

Example 4

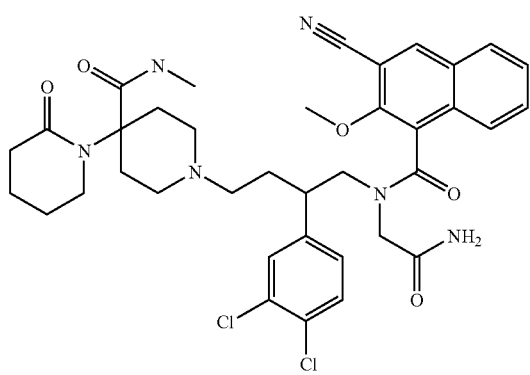
Method A
| | |
|---|---|
| Salt form | citrate salt |
| Melting point | 175–180° C. |
| NMR | 8.6 (m, 1H), 8.2–6.8 (m, 7H), 4.0(twopeaks, 3H), 1.8(br., 4H). |
| Mass Spec | 721 (M + 1) |
Example 5
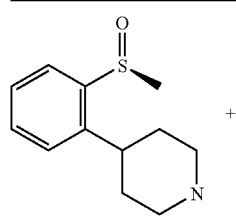
+
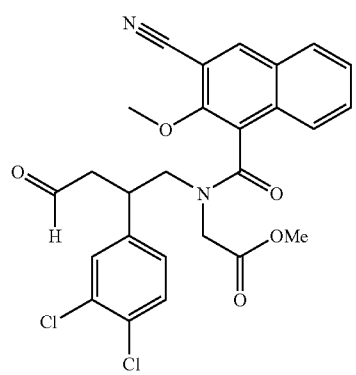
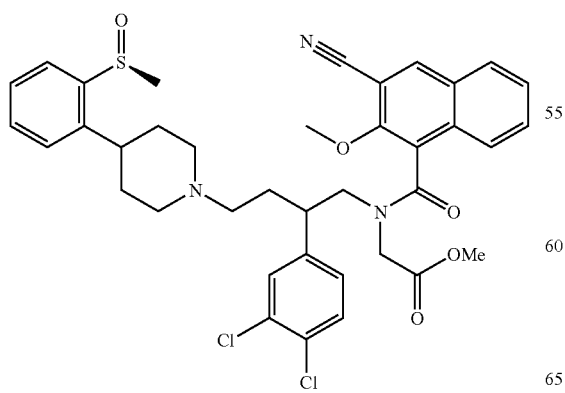
-continued
Method A
| | |
|---|---|
| Salt form | citrate salt |
| Melting point | 130–135° C. |
| NMR | 8.3(m, 1H), 8.0–6.6(m, 11H), 4.1(three peaks, 3H), 3.8 (two peaks, 3H), 3.6(s, 3H), 1.8(br., 2H). |
| Mass Spec | 720 (M + 1) |
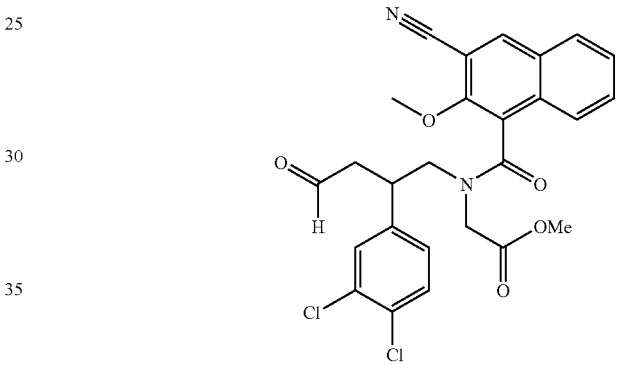
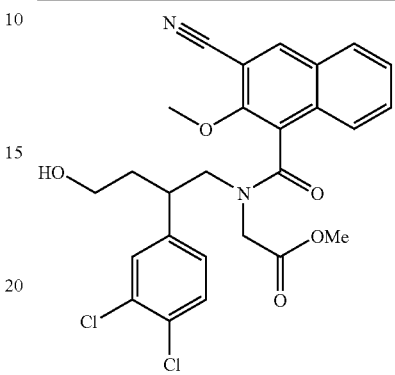
Method A
| | |
|---|---|
| NMR | 9.6(three peaks, 1H), 8.3(m, 1H), 8.0–6.6(m, 7H), 4.1(s, 3H), 3.8(m, 3H), 2.6(m, 2H). |
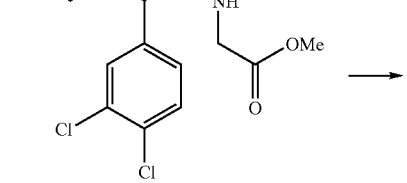
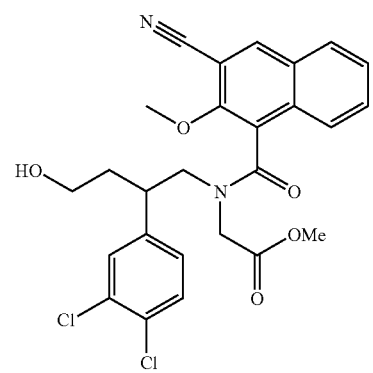

| | |
|---|---|
| NMR | 8.3(m,1H), 8.0–6.6(m, 7H), 4.1(m, 3H), 3.8(m, 3H), 2.6(m, 2H). |
| Mass Spec | 515 (M + 1) |
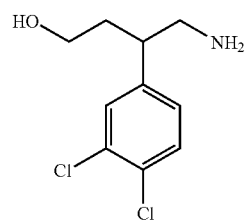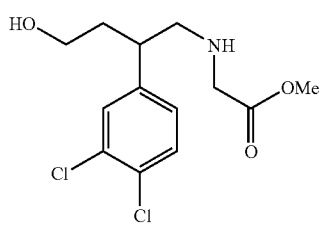
Method A
| | |
|---|---|
| Mass Spec | 322 (M + 1) |
Example 6
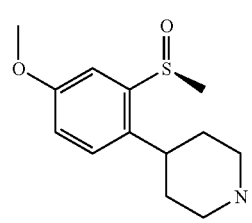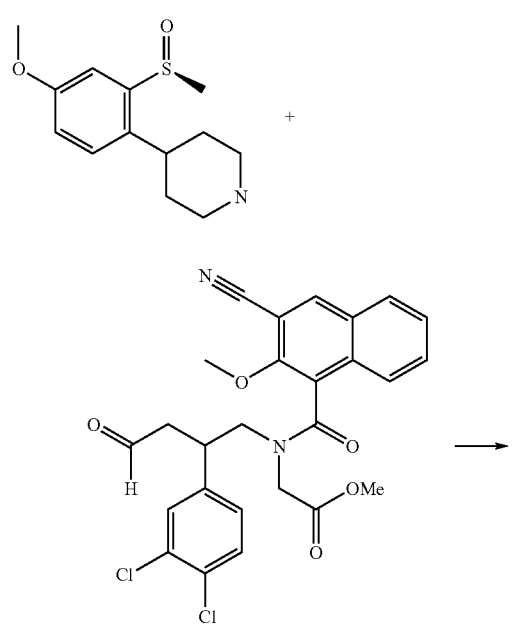
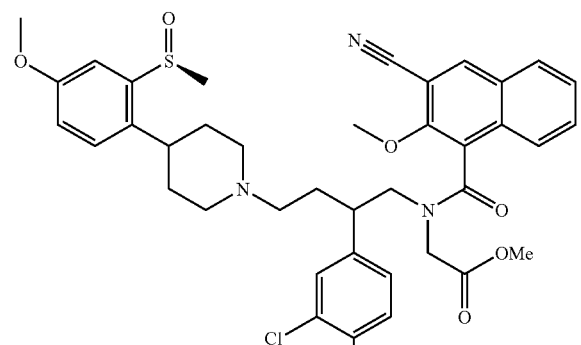
Method A
| | |
|---|---|
| Salt form | citrate |
| Melting point | 120–130° C. |
| NMR | 8.3 (m, 1H), 7.9–6.6 (m, 10H), 4.0(m, 3H), 3.8(m, 3H), 3.6(m, 3H), 1.8(br., 2H). |
| Mass Spec | 750 (M + 1) |
Example 7
Method E
| | |
|---|---|
| Salt form | citrate |
| Melting point | 120–125° C. |
| NMR | 8.3 (m, 1H), 7.9–6.4 (m, 10H), 4.0(m, 3H), 3.8(m, 3H), 3.6(m, 3H), 1.8(br., 2H). |
| Mass Spec | 735 (M + 1) |

Example 8
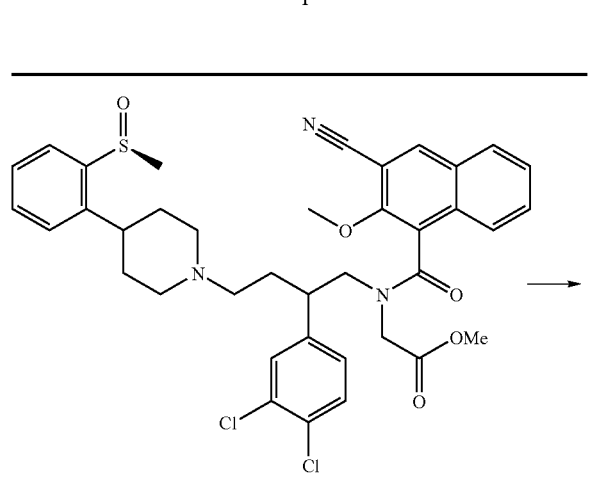
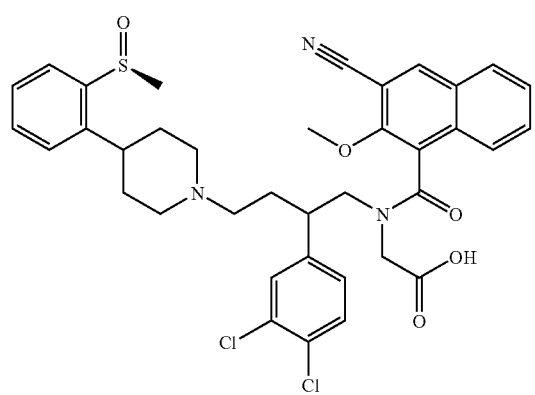
Hydrolysis with 1N NaOH in methanol and purification by HPLC.
| | |
|---|---|
| Salt form | citrate |
| Melting point | 128–165° C. |
| NMR | 8.2 (s, 1H), 8.1 (d, J=3 Hz, 1H), 7.9–6.6 (m, 12H), 4.2 (m, 3H), 3.6 (m, 3H), 1.8 (br., 4H). |
| Mass Spec | 735 (M + 1) |
Example 9
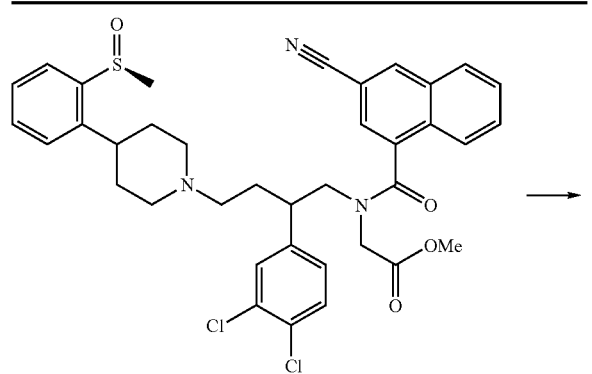
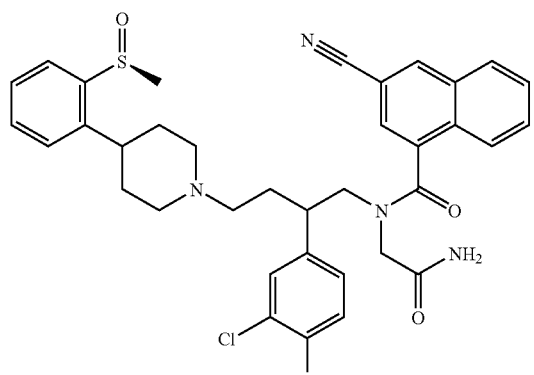
Method E
| | |
|---|---|
| Salt form | citrate |
| Melting point | 155–166° C. |
| NMR | 8.6 (m, 1H), 8.2–6.4 (m, 12H), 3.6 (m, 3H), 1.8 (br., 8H). |
| Mass Spec | 675 (M + 1) |
Example 10
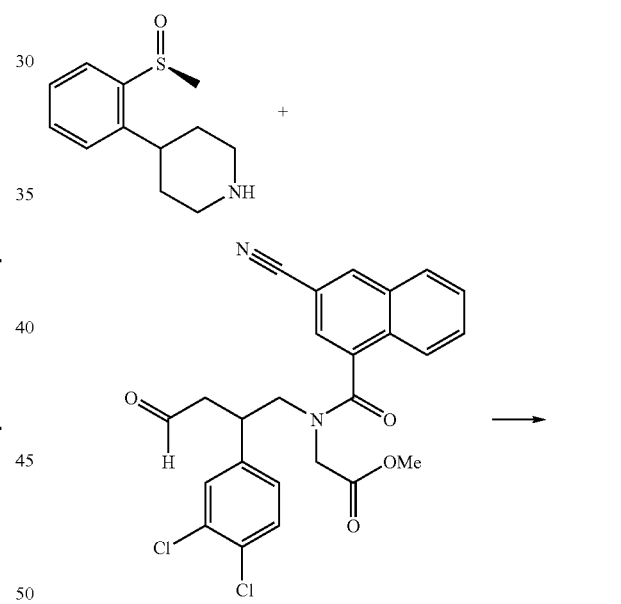
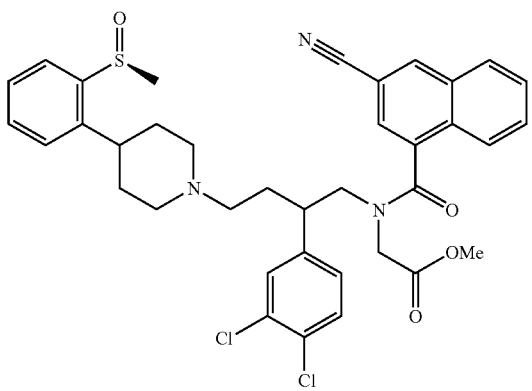

-continued
Method A.
| NMR | 8.2 (m, 1H), 8.0–6.6 (m, 12H), 2.6 (m, 6H), 1.8(br., 8H). |
|---|---|
| Mass Spec | 690 (M + 1) |
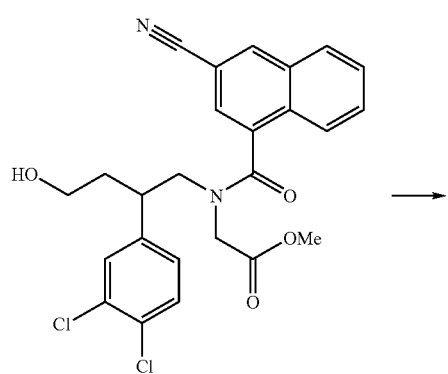
Method C.
| NMR | 9.7 (two peaks, 1H), 8.2 (m, 1H), 8.0–6.4 (m, 8H), 3.8 (m, 2H), 2.6 (br., 2H). |
|---|---|
| Mass Spec | 483 (M + 1) |
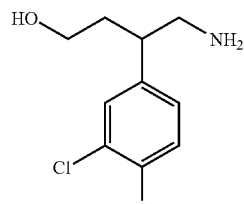
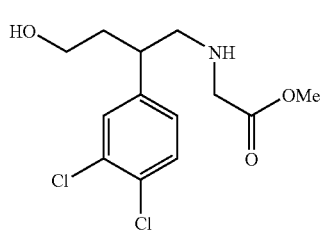
-continued
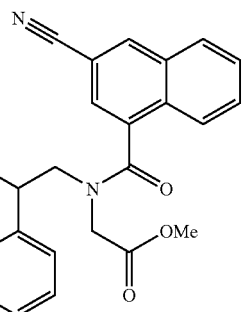
Method C and then B
| NMR | 8.2 (m, 1H), 8.0–6.6 (m, 8H), 3.8 (m, 2H), 3.7–3.4 (m, 6H), 3.2 (br., 2H). |
|---|---|
| Mass Spec | 485 (M + 1) |
Example 11
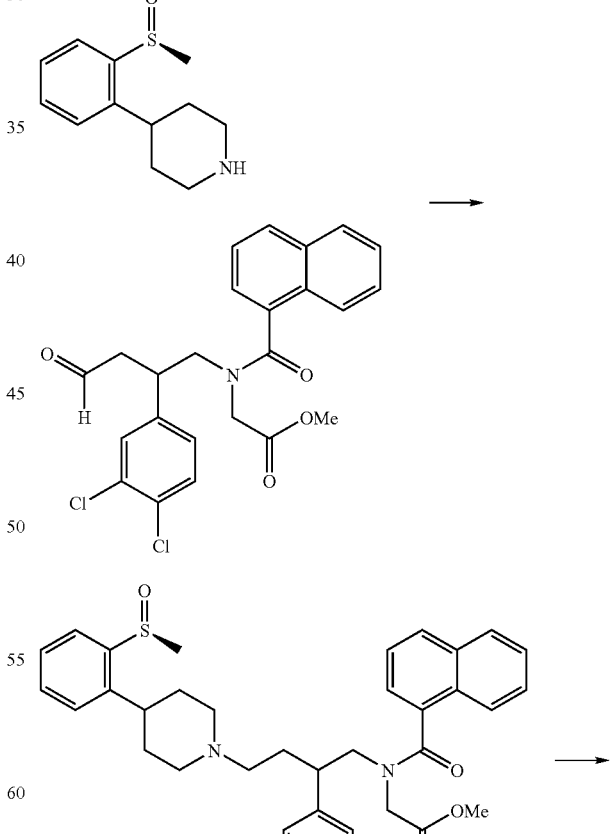

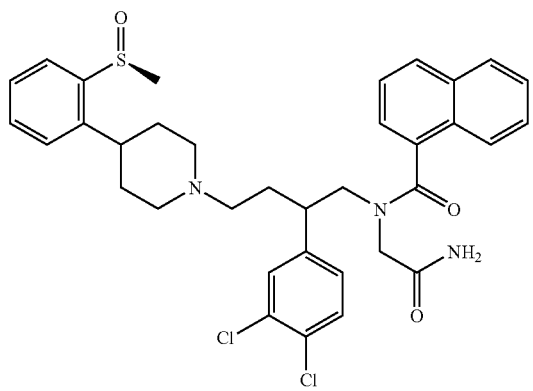
Method A, E.
| | |
|---|---|
| Salt form | citrate |
| Melting point | 145–162° C. |
| NMR | 8.0–6.4 (m, 14H), 3.5 (m, 3H), 1.8 (br., 8H). |
| Mass Spec | 650 (M + 1) |
Example 12
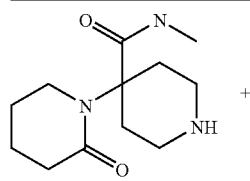 +
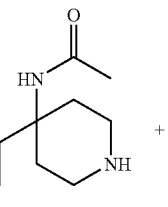
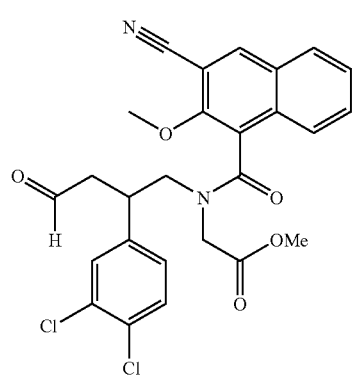
Method A.
| | |
|---|---|
| Salt form | citrate |
| Melting point | 130–162° C. |
| NMR | 8.6 (m, 1H), 8.2–6.6 (m, 7H), 3.9 (m, 3H), 3.8 (m, 3H), 1.6 (m, 4H). |
| Mass Spec | 736 (M + 1) |
Example 13
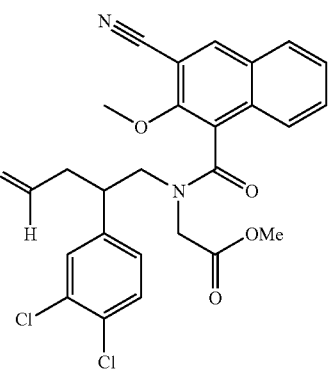 +
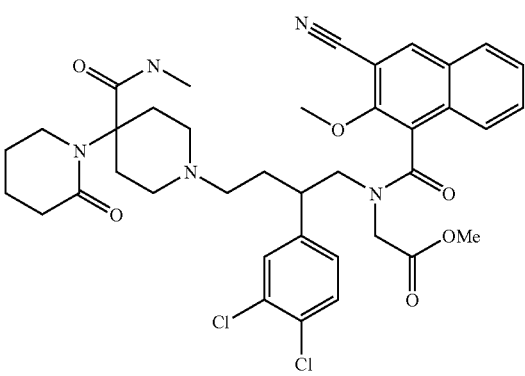
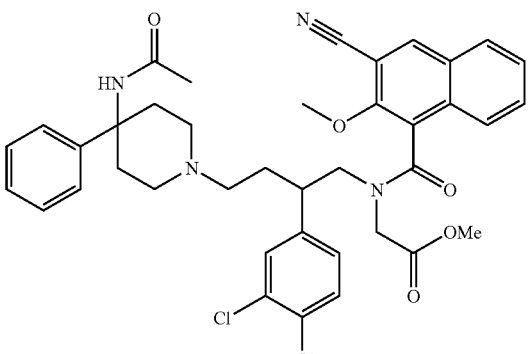
Method A.
| | |
|---|---|
| Salt form | citrate |
| Melting point | 120–165° C. |
| NMR | 8.6 (m, 1H), 8.1–6.6 (m, 12H), 3.9 (m, 3H), 3.8 (m, 3H), 1.8 (m, 4H). |
| Mass Spec | 715 (M + 1) |

Example 14
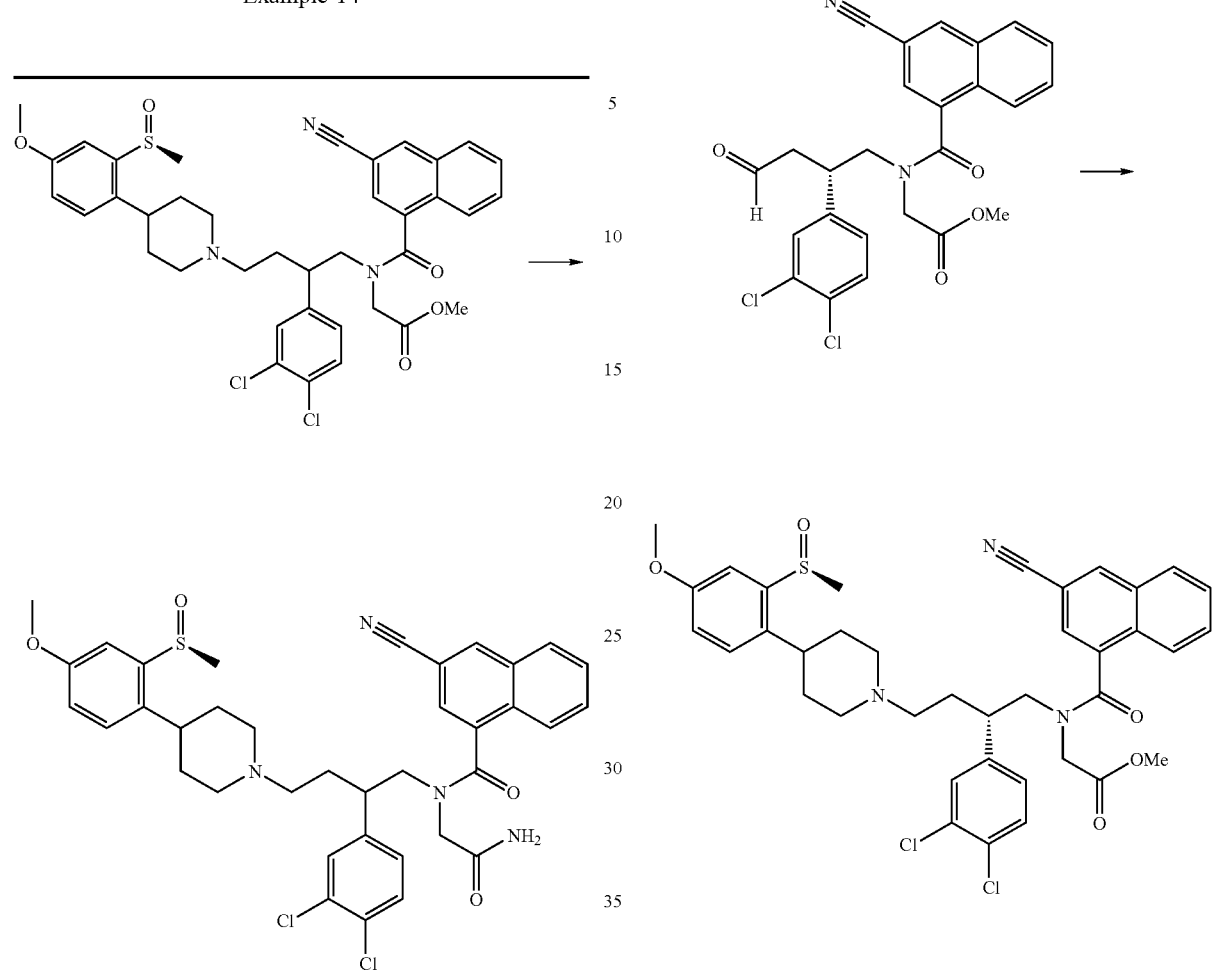
Method A.
| | |
|---|---|
| Salt form | citrate |
| Melting point | 135–155° C. |
| NMR | 8.6 (m, 1H), 8.1–6.6 (m, 11H), 3.9 (s, 3H), 3.8 (m, 3H), 1.8 (m, 4H). |
| Mass Spec | 705 (M + 1) |
Example 15
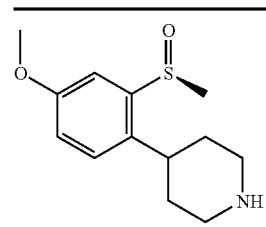 +
Method A.
| | |
|---|---|
| NMR | 8.2 (m, 1H), 7.9–6.5 (m, 11H), 3.8 (s,3H), 2.6 (m, 3H), 1.8 (m, 4H). |
| Mass Spec | 720 (M + 1) |
Example 16

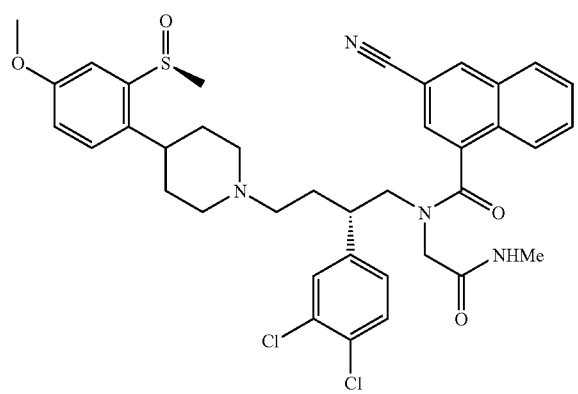
Method similar to method E was used except that methylamine was used instead of ammonia.
| | |
|---|---|
| Salt form | citrate |
| Melting point | 115–140° C. |
| NMR | 8.7 (m, 1H), 8.2–6.7 (m, 10H), 3.95 (m, 3H), 3.8 (m, 311), 1.8 (m, 4H). |
| Mass Spec | 749 (M + 1) |
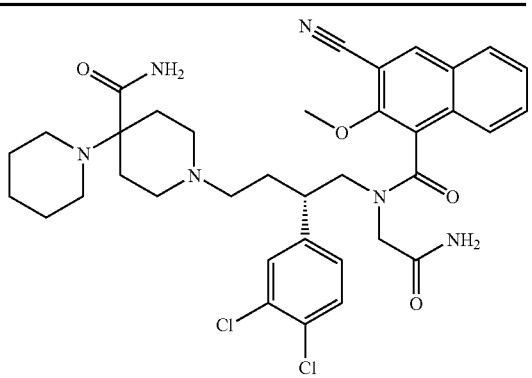
Method A, E.
| | |
|---|---|
| Salt form | citrate |
| Melting point | 130–160° C. |
| NMR | 8.6(m, 1H), 8.2–6.7(m, 7H), 3.95(m, 3H), 3.5(m, 3H), 13(m, 10H). |
| Mass Spec | 693(M + 1) |
Example 17
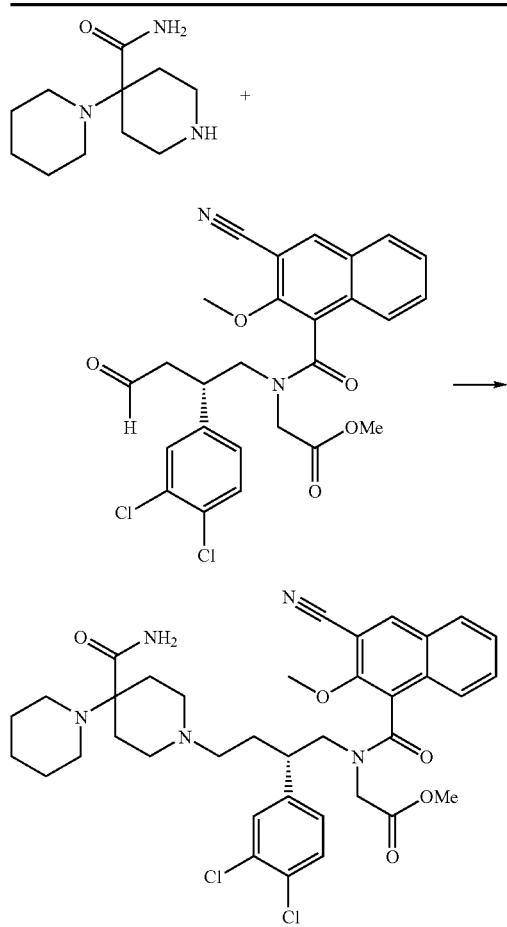
Example 18
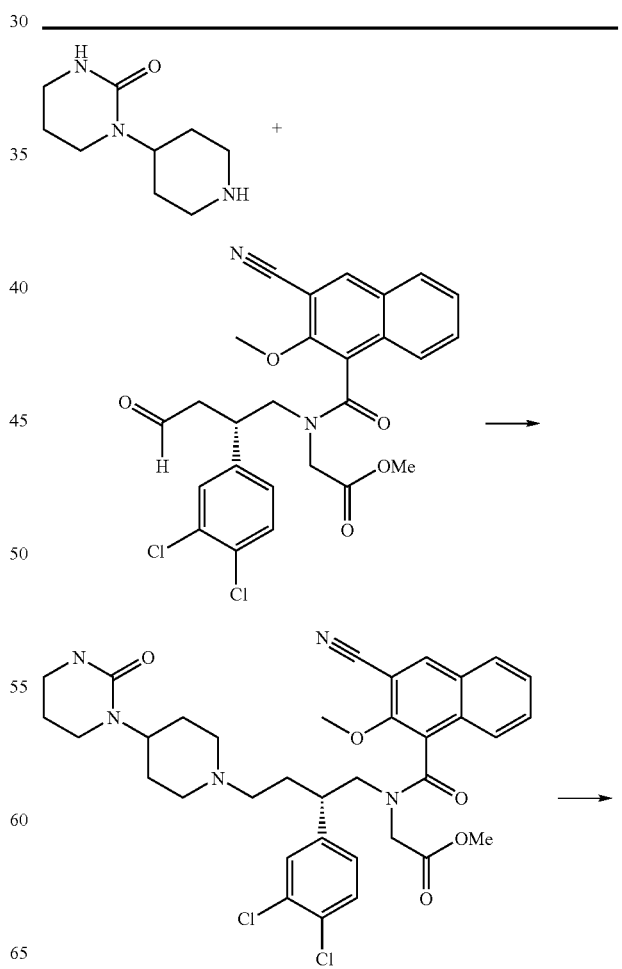

-continued
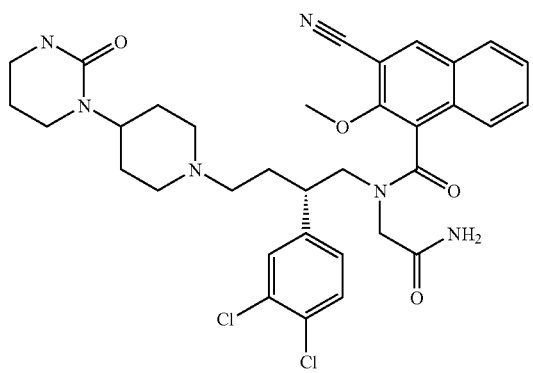
Method A, E.
| Salt form | citrate |
|---|---|
| Melting point | 125–165° C. |
| NMR | 8.6(m, 1H), 8.2–6.7(m, 7H), 3.95(m, 3H), 3.5(m, 3H), 1.3(m, 10H). |
| Mass Spec | 665(M + 1) |
Example 19
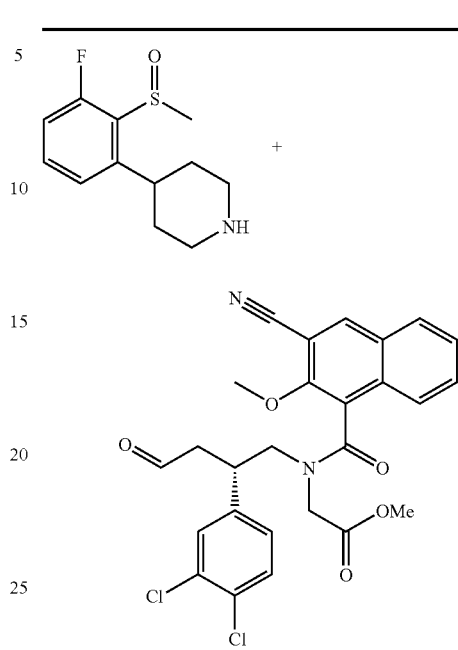
A procedure similar to Method E was used except that instead of ammonia hydrazine hydrate was used.
| Salt form | citrate |
|---|---|
| Melting point | 135–165° C. |
| NMR | 9.2(m 1H), 8.6(m, 1H), 8.2–6.7(m, 10H), 3.95(m, 3H), 3.8(m, 3H), 1.6(m, 4H). |
| Mass Spec | 750(M + 1) |
Example 20
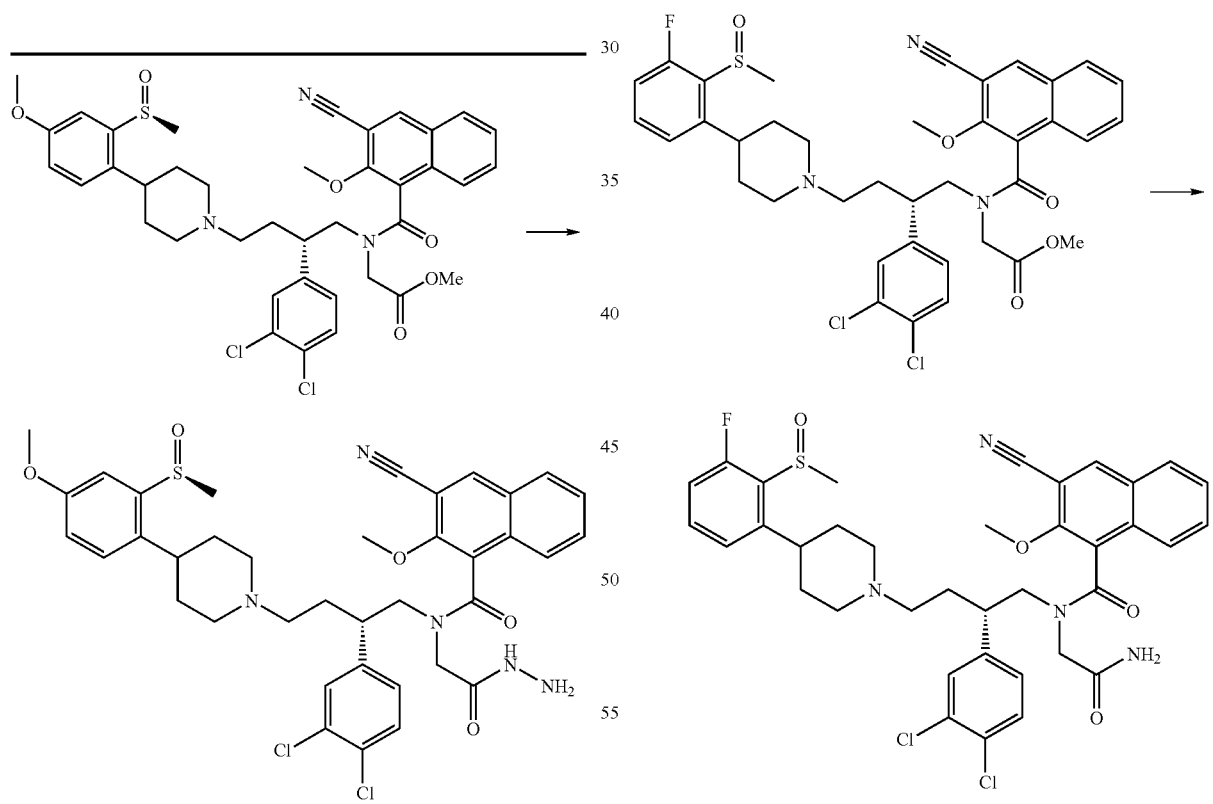
Method A, E
| Salt form | citrate |
|---|---|
| Melting point | 135–165° C. |
| NMR | 8.7(m, 1H), 8.2–6.7(m, 10H), 3.95(m, 3H), 1.7(m, 4H). |
| Mass Spec | 723(M + 1) |

Example 21
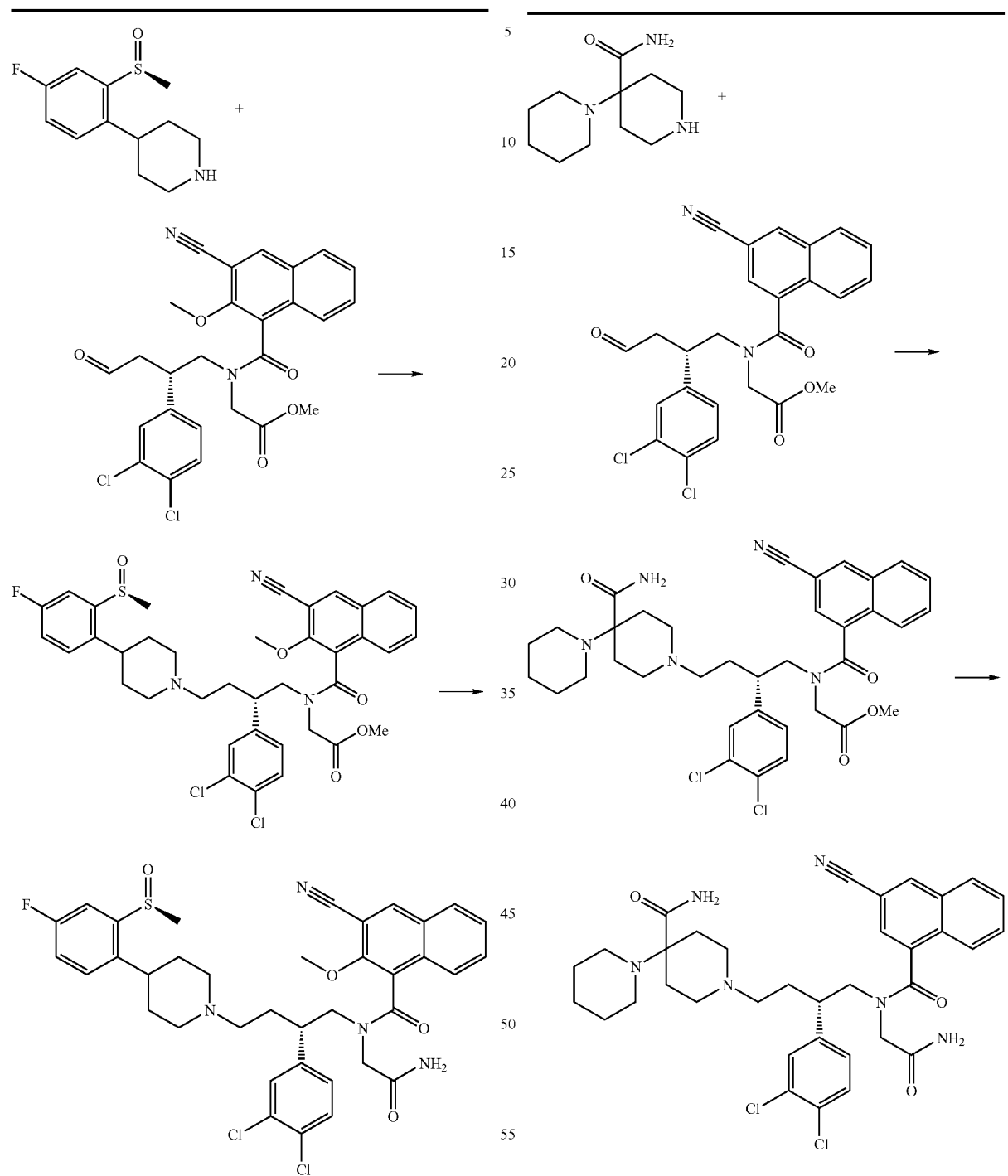
Method A, E.
| | |
|---|---|
| Salt form | citrate |
| Melting point | 125–140° C. |
| NMR | 8.7(m, 2H), 8.0(d, J=4Hz, 1H), 7.6–7.1(m, 10H), 3.95(s, 3H), 1.8(m, 6H). |
| Mass Spec | 723(M + 1) |
Example 22
Method A, E.
| | |
|---|---|
| Salt form | citrate |
| Melting point | 140–150° C. |
| NMR | 8.7(m, 2H), 8.1(d, J=4Hz, 1H), 7.8–7.0(m, 8H), 3.8–3.2(m, 10H), 1.4(m, 4H). |
| Mass Spec | 663(M + 1) |

37
Example 23
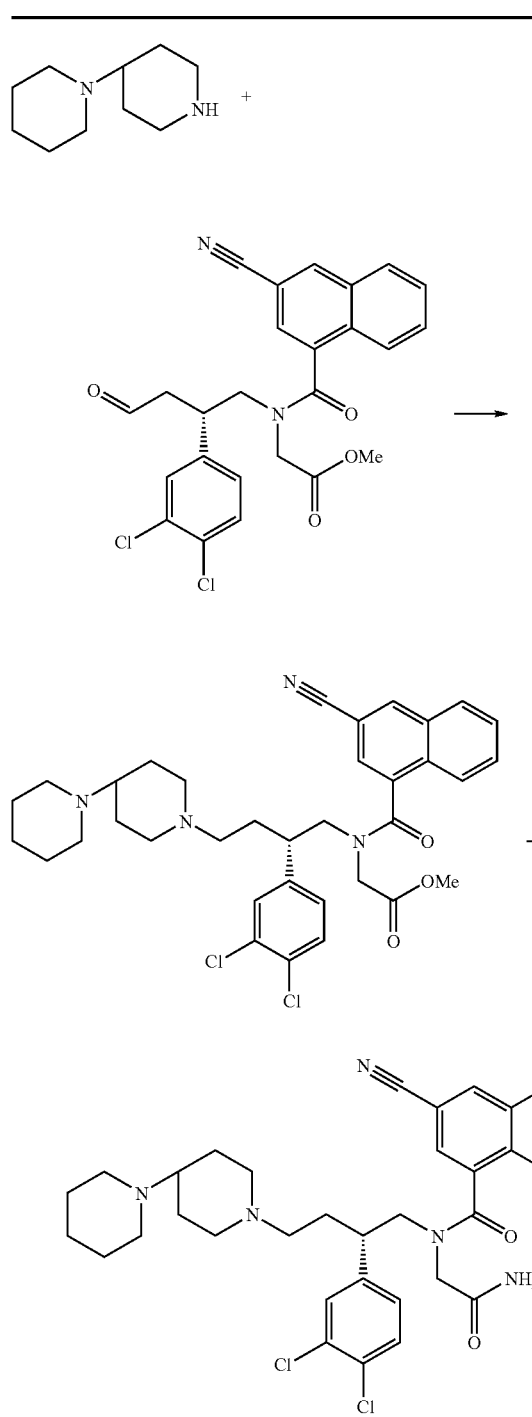
Method A, E.
| | |
|---|---|
| Salt form | citrate |
| Melting point | 135–140° C. |
| NMR | 8.6(m, 2H), 8.4–6.4(m, 9H), 2.0–1.4(m, 10H). |
| Mass Spec | 620(M + 1) |
38
Example 24
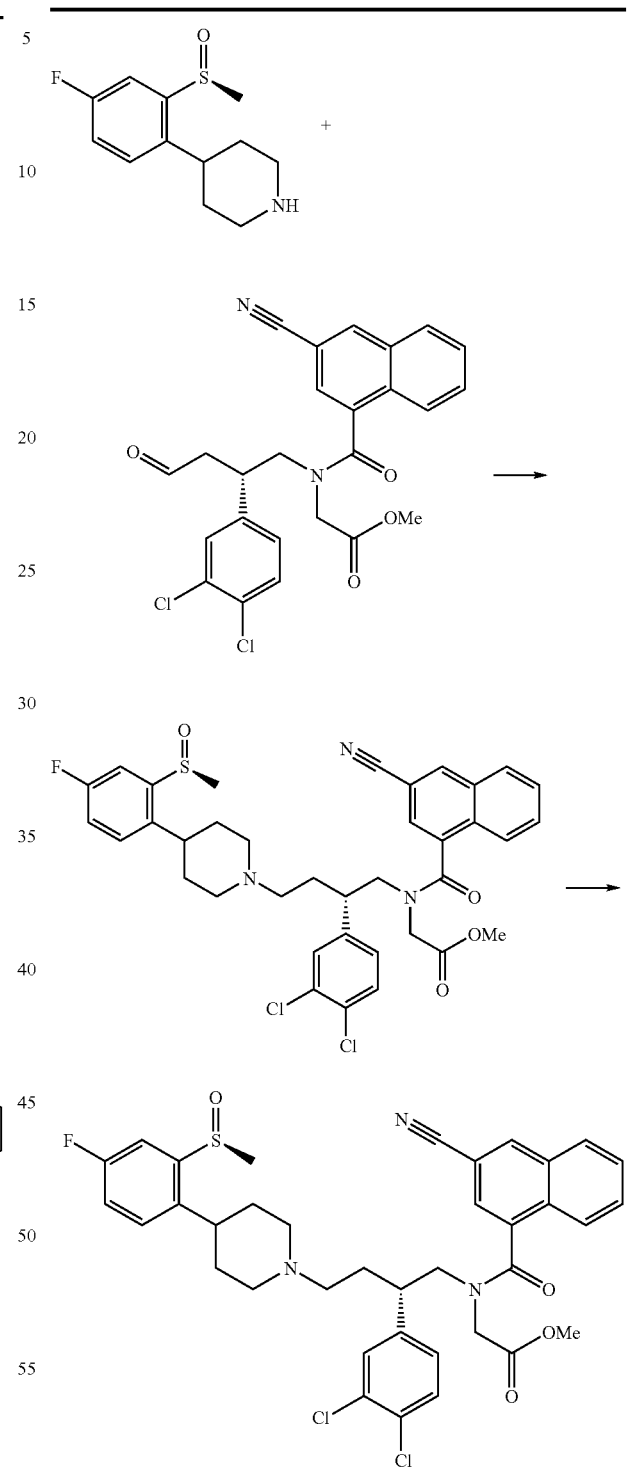
Method A, E.
| | |
|---|---|
| Salt form | citrate |
| Melting point | 140–165° C. |
| NMR | 8.6–6.4(m, 12H), 3.6(m, 3H), 1.8–1.6(m, 4H). |
| Mass Spec | 693(M + 1) |

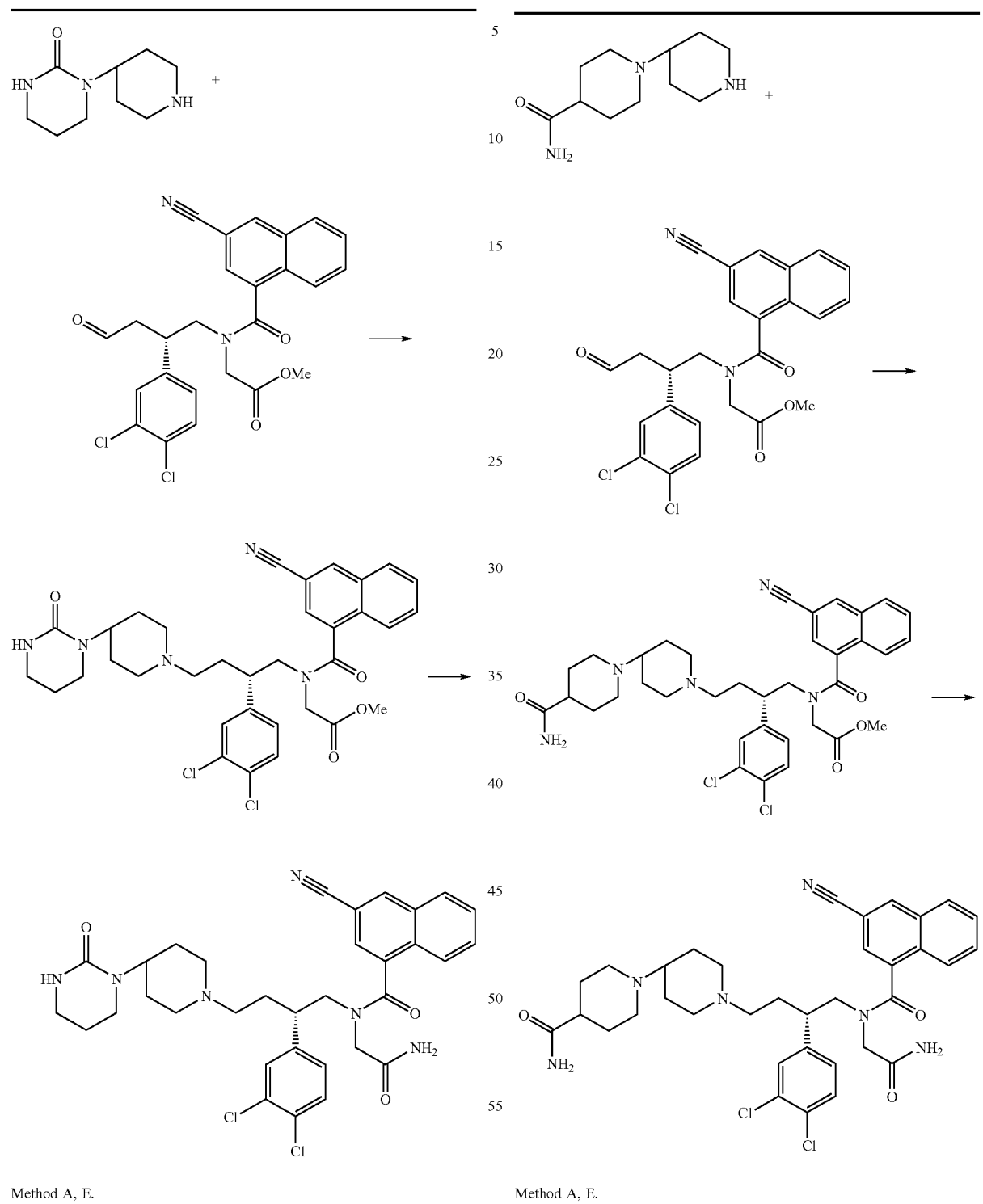
| | Example 25 | | Example 26 |
|---|---|---|---|
| Salt form | citrate | Salt form | citrate |
| Melting point | 165–170° C. | Melting point | 160–205° C. |
| NMR | 8.6–6.2(m, 9H), 1.8–1.4(m, 8H) | NMR | 8.6–6.5(m, 9H), 1.7(m, 4H). |
| Mass Spec | 635(M + 1) | Mass Spec | 580(M + 1) |
Method A, E. (Example 25)
Method A, E. (Example 26)

Example 27
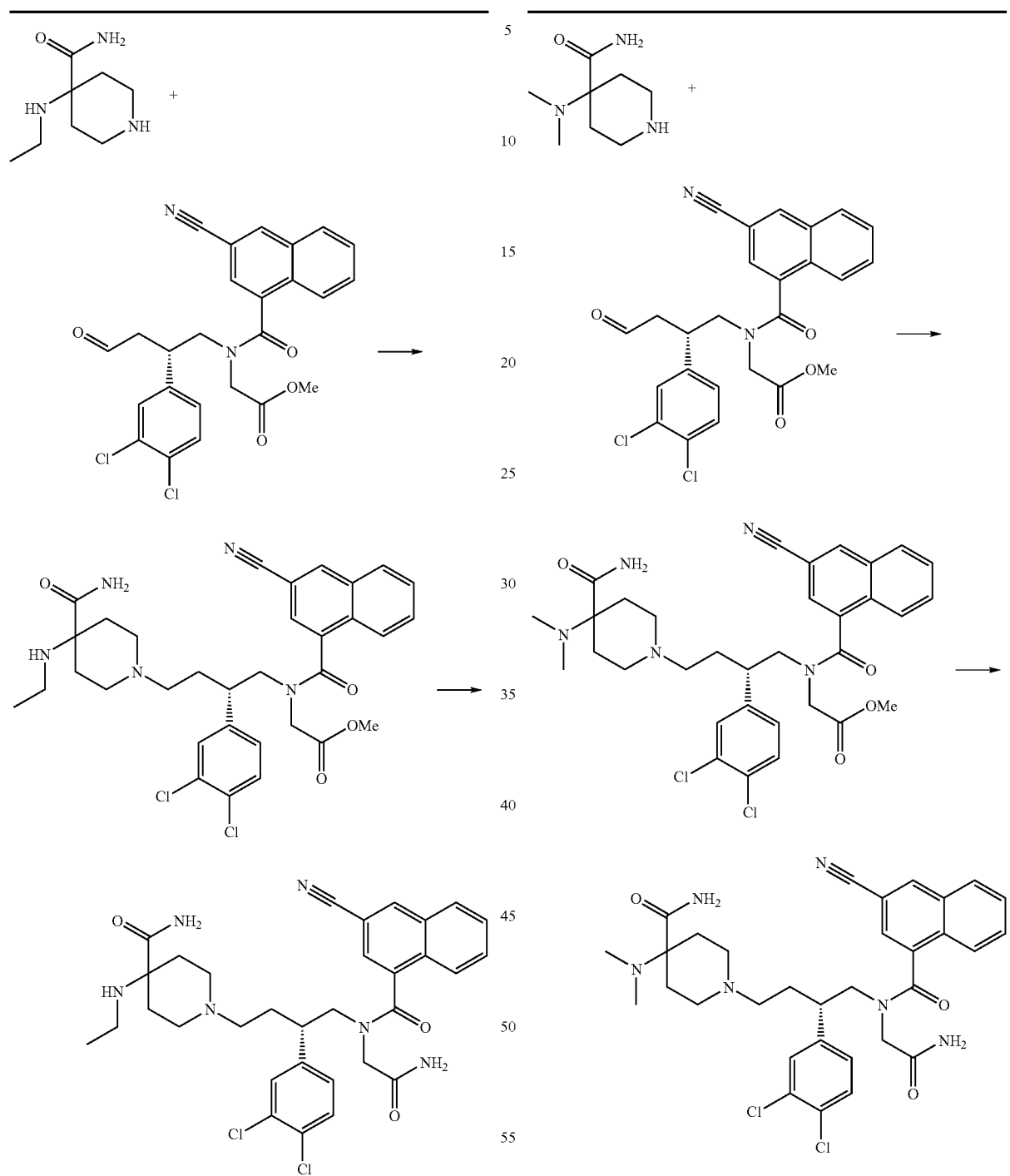
Method A, E.
| | |
|---|---|
| Salt form | citrate |
| Melting point | 140–185° C. |
| NMR | 8.6(m, 1H), 8.1(m, 1H), 7.8–6.5(m, 9H), 1.1(m, 3H). |
| Mass Spec | 623(M + 1) |
Example 28
Method A, E.
| | |
|---|---|
| Salt form | citrate |
| Melting point | 125–155° C. |
| NMR | 8.6(m, 1H), 8.1(m, 1H), 7.8–6.5(m, 9H), 2.2(two peaks, 6H). |
| Mass Spec | 623(M + 1) |

Example 29
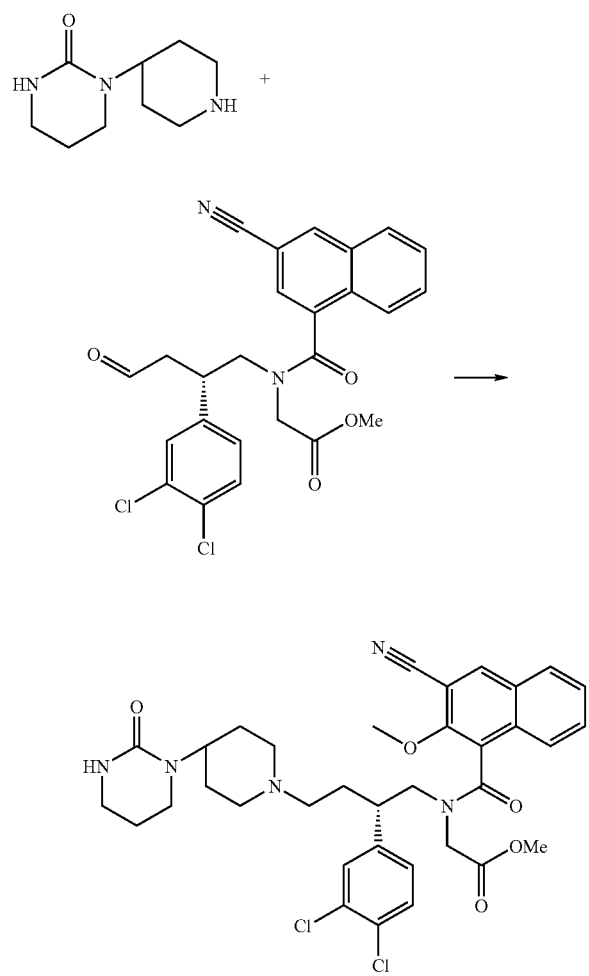
Method A.
| | |
|---|---|
| Salt form | citrate |
| Melting point | 150–160° C. |
| NMR | 8.7(m, 1H), 8.0(m, 1H), 7.8–6.2(m, 7H), 1.8(m, 6H). |
| Mass Spec | 680(M + 1) |
Example 30
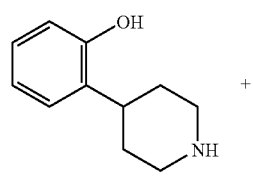
-continued
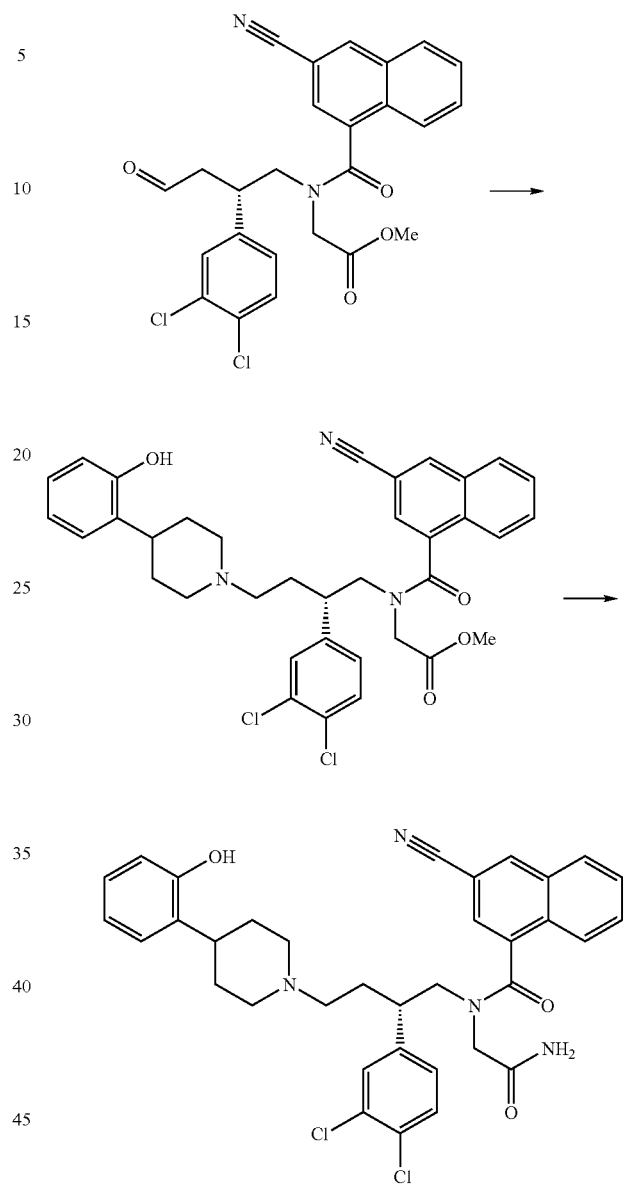
Method A, E.
| | |
|---|---|
| Salt form | citrate |
| Melting point | 220–225° C. |
| NMR | 9.4(m, 1H), 8.6–6.4(m, 13H), 1.8(m, 6H). |
| Mass Spec | 629(M + 1) |
Example 31
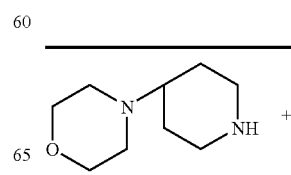

45
-continued
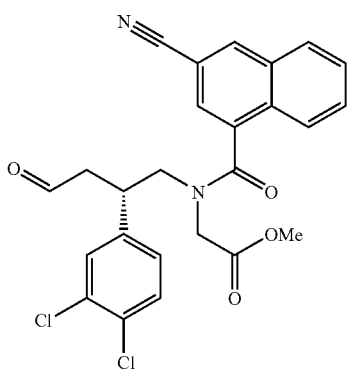
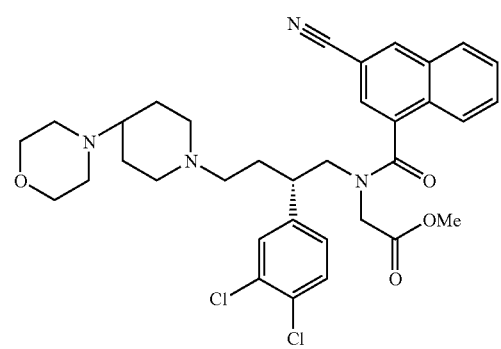
| Method A, E. | |
|---|---|
| Salt form | citrate |
| Melting point | 170–175° C. |
| NMR | 8.6(m, 1H), 8.1(m, 1H), 7.8–6.5(m, 9H), 1.6(m, 2H). |
| Mass Spec | 539(M + 1) |
46
Example 32
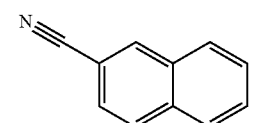 + 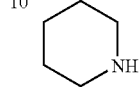
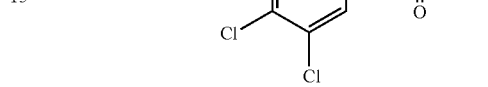
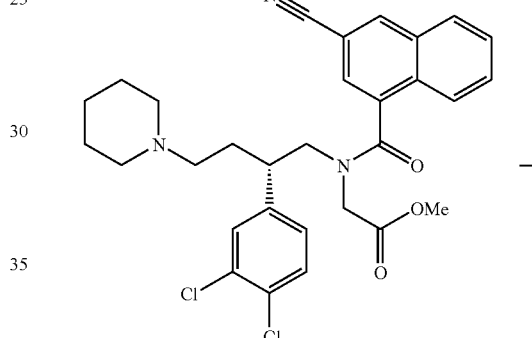
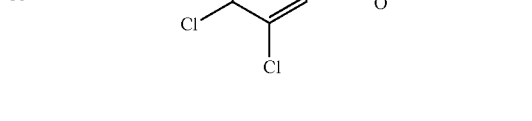
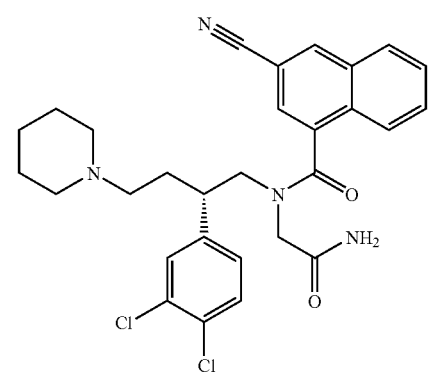
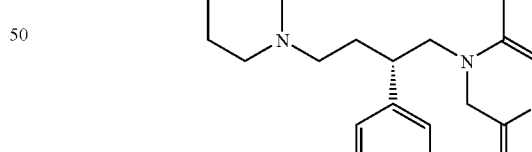
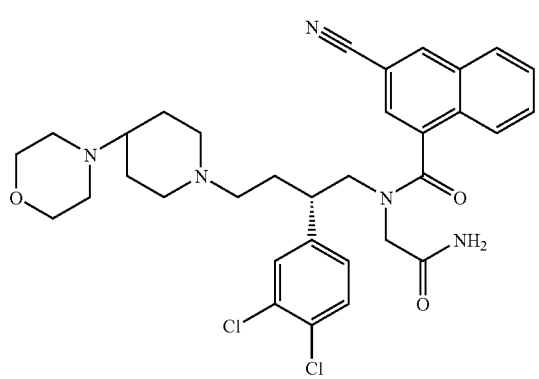
| Method A, E. | |
|---|---|
| Salt form | citrate |
| Melting point | 170–175° C. |
| NMR | 8.6(m, 1H), 8.1(m, 1H), 7.8–6.4(m, 9H), 1.6(m, 6H). |
| Mass Spec | 537(M + 1) |

Example 33
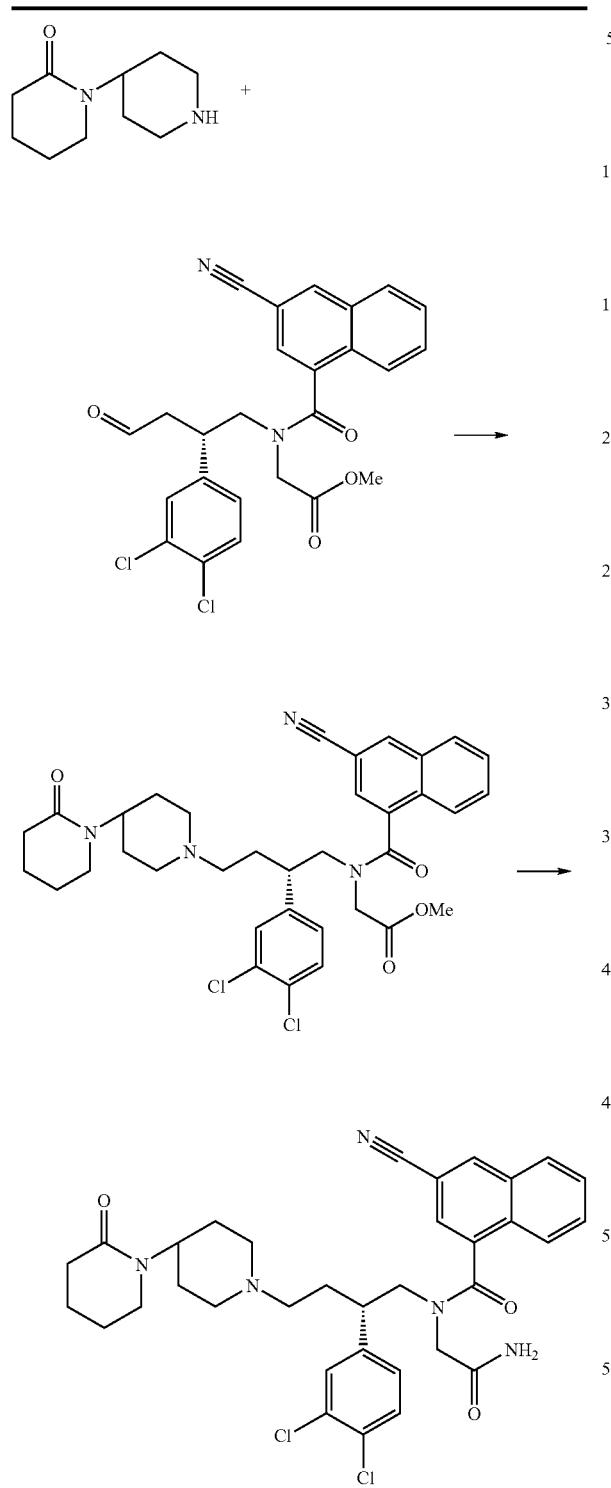
Method A, E.
| | |
|---|---|
| Salt form | citrate |
| Melting point | 170–175° C. |
| NMR | 8.6(m, 1H), 8.05(m, 1H), 7.8–6.5(m, 8H), 1.6(m, 8H). |
| Mass Spec | 634(M + 1) |
Example 34
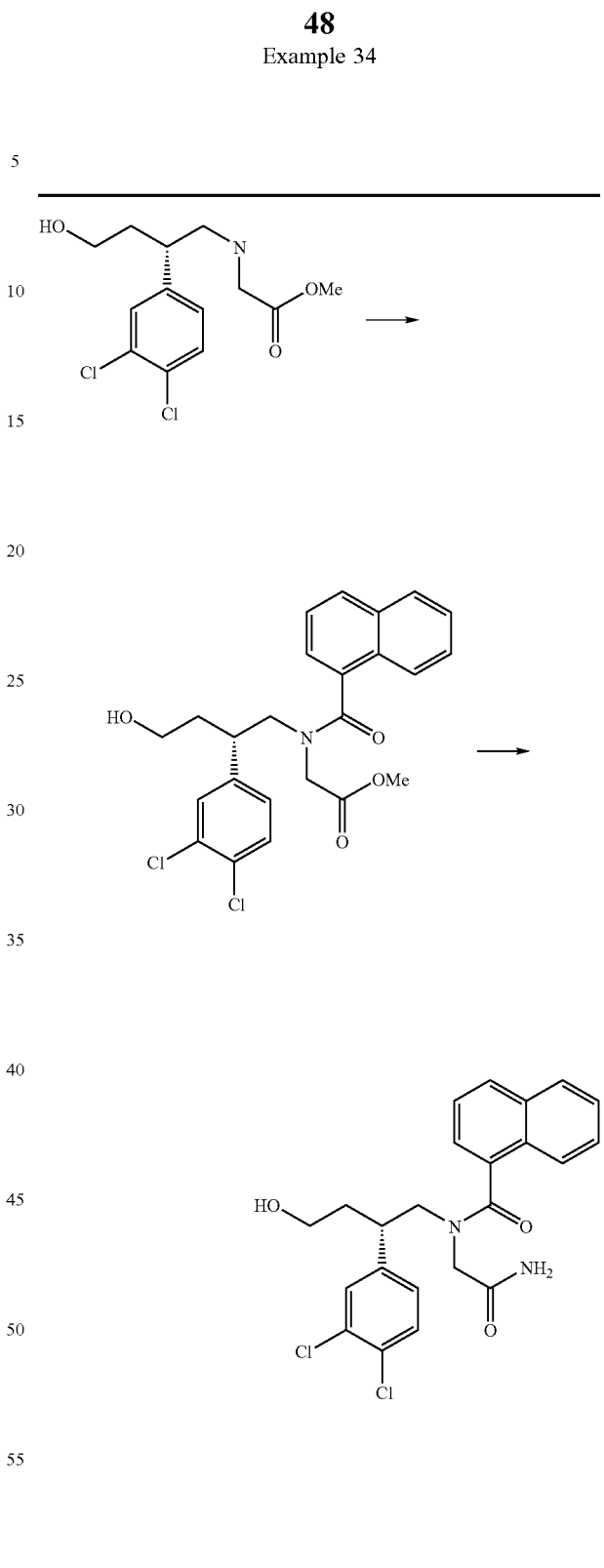
Method B, E.
| | |
|---|---|
| Melting point | 77–85° C. |
| NMR | 8.3–6.3(m, 11H), 1.8(m, 2H), 1.4(m, 1H). |
| Mass spec | 445(M + 1) |

Example 35

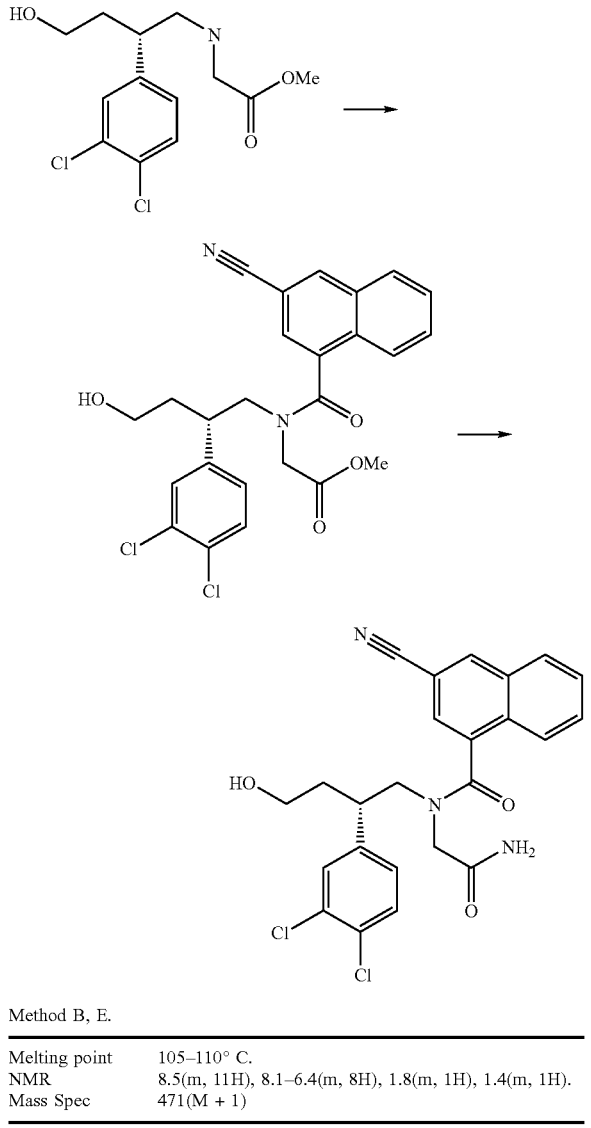

Method B, E.

| | |
|---|---|
| Melting point | 105–110° C. |
| NMR | 8.5(m, 11H), 8.1–6.4(m, 8H), 1.8(m, 1H), 1.4(m, 1H). |
| Mass Spec | 471(M + 1) |

Example 36

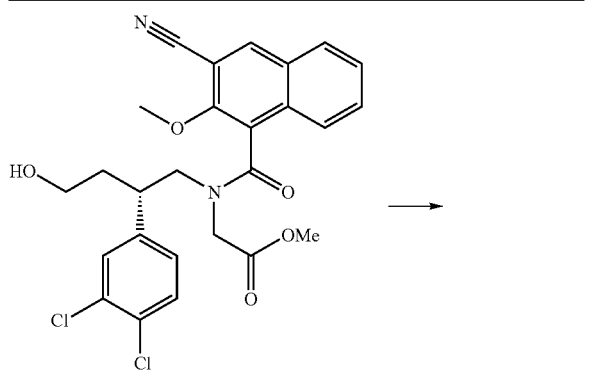

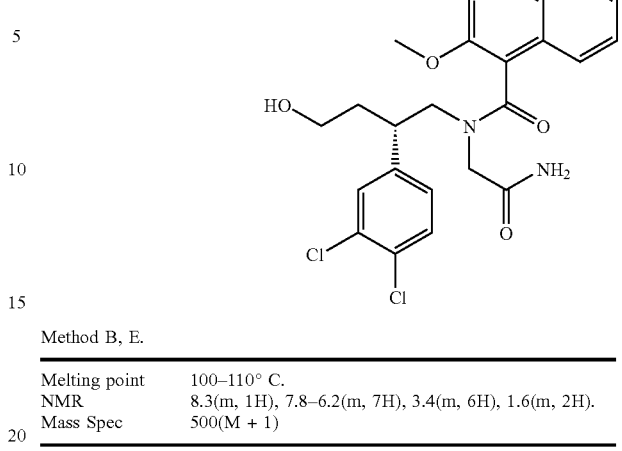

Method B, E.

| | |
|---|---|
| Melting point | 100–110° C. |
| NMR | 8.3(m, 1H), 7.8–6.2(m, 7H), 3.4(m, 6H), 1.6(m, 2H). |
| Mass Spec | 500(M + 1) |

Example 37

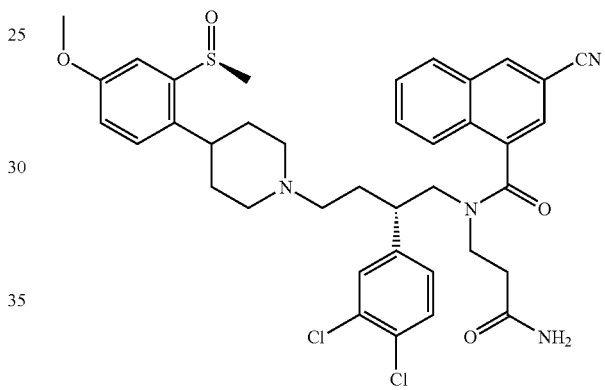

N-[2-(3,4-Dichlorophenyl)-4-[4-[4-methoxy-(S)-2-methylsulfinylphenyl]-1-piperidinyl]-butyl]-N-[(2-carboxamide)ethyl]-3-cyano-1-naphthamide citrate N-[2-(3,4-Dichlorophenyl)-4-[4-[4-methoxy-(S)-2-methylsulfinylphenyl]-1-piperidinyl]butyl]-N-[(2-carboxyethyl)ethyl]-3-cyano-1-naphthamide was dissolved in 12 mL MeOH (2.0 M in NH$_3$) and heated to 70° C. in a sealed tube for 20 h. Mixture was cooled, MeOH was evaporated, product was purified by chromatography (100:1→>20:1, DCM:MeOH w/0.5% conc. NH$_{3(aq)}$) and converted to the citrate salt; MS: m/z 719 (M+); $^1$H NMR (DMSO-d$_6$) δ 8.64 (s), 8.61 (s), 8.19–8.03 (m), 7.88–6.75 (m), 6.54 (s), 6.32 (d), 4.60 (m), 3.82 (s), 3.81 (s), 3.95–1.50.

Intermediates were prepared as follows:

4-[2-(3,4-Dichlorophenyl)]-pentenal

4-[2-(3,4-Dichlorophenyl)]-pentenol (10.60 g) was reacted with oxalyl chloride/DMSO under standard swern oxidizing conditions in DCM (750 mL) to afford 4-[2-(3,4-dichlorophenyl)]-pentenal (9.76 g crude) as a liquid after aqueous extraction from DCM; $^1$H NMR (CDCl$_3$) δ 9.67 (m), 7.46 (d), 7.30 (d), 7.03 (dd), 5.75–5.55 (m), 5.20–4.90 (m), 3.60 (t), 2.83 (dt), 2.47 (dt).

[2-(3,4-Dichlorophenyl)]-N-[(2-carboxyethyl)ethyl]-4-pentenamine

β-Alanine ethyl ester hydrochloride (1.10 g) was stirred with 30 mL MeOH and 1.1 mL Et$_3$N until all had dissolved.

To this was added (1.59 g) 4-[2-(3,4-dichlorophenyl)]-pentenal followed by 1.1 mL HOAc. Mixture was stirred for 1.5 h, 0.75 g of NaCNBH$_3$ was added, and mixture was stirred for 18 h. At this point 100 mL of 20% K$_2$CO$_{3\,(aq)}$ was added, MeOH was evaporated, and aqueous residue was extracted with DCM. Extracts were dried over Na$_2$SO$_4$, filtered, and concentrated to give an oil (2.09 g); MS: m/z 330 (M+); $^1$H NMR (CDCl$_3$) δ 7.38 (d), 7.28 (d), 7.03 (dd), 5.72–5.50 (m), 5.20–4.78 (m), 4.10 (q), 3.09 (q), 2.95–2.70 (m), 2.60–2.30 (m), 1.36 (t), 1.21 (t).

N-[2-(3,4-Dichlorophenyl)-4-pentenyl]-N-[(2-carboxyethyl)ethyl]-3-cyano-1-naphthamide 1-Naphthoyl chloride (0.97 g) was combined with [2-(3,4-dichlorophenyl)]-N-[(2-carboxyethyl)ethyl]-4-pentenamine (1.49 g) and triethyl amine under standard acylation conditions to afford N-[2-(3,4-dichlorophenyl)-4-pentenyl]-N-[(2-carboxyethyl)ethyl]-3-cyano-1-naphthamide (0.56 g) as a solid after purification by chromatography (5:4:1 Hexane:DCM:EtOAc); MS: m/z 509 (M+); $^1$H NMR (CDCl$_3$) δ 8.25–8.10 (m), 7.95–7.05 (m), 6.98–6.80 (m), 6.78–6.62 (m), 6.60–6.41 (m), 5.77–5.58 (m), 5.35–4.72 (m), 4.30–1.90 (m), 1.40–1.15 (m).

N-[2-(3,4-Dichlorophenyl)-4-oxobutyl]-N-[(2-carboxyethyl)ethyl]-3-cyano-1-naphthamide To a stirred slurry of N-[2-(3,4-dichlorophenyl)-4-pentenyl]-N-[(2-carboxyethyl)ethyl]-3-cyano-1-naphthamide (0.56 g) and NaIO$_4$ (0.82 g) in 60 mL 1:1 THF:H$_2$O was slowly added 0.55 mL OsO$_4$ solution (4% w/w in H$_2$O). Mixture was stired for 18 h, 10 mL sat'd Na$_2$S$_2$O$_{3(aq)}$ was added, THF was evaporated, and aqueous residue was extracted with DCM. Extracts were dried over Na$_2$SO$_4$, filtered, and concentrated. This gave 0.26 g of N-[2-(3,4-dichlorophenyl)-4-oxobutyl]-N-[(2-carboxyethyl)ethyl]-3-cyano-1-naphtharide after purification by chromatography (5:4:1 Hexane:DCM:EtOAc); MS: m/z 511 (M+); $^1$H NMR (CDCl$_3$) δ 9.79 (s), 9.56 (s), 9.55 (s), 8.26–8.19 (m), 8.00–7.82 (m), 7.79–7.20 (m), 7.00–6.90 (m), 6.81–6.72 (m), 6.68–6.55 (m), 4.45 (t), 4.30–2.78 (m), 2.60–2.25 (m), 1.40–1.12 (m).

N-[2-(3,4-Dichlorophenyl)-4-[4-[4-methoxy-(S)-2-methylsulfnylphenyl]-1-piperidinyl]-butyl]-N-[(2-carboxyethyl)ethyl]-3-cyano-1-naphthamide Using standard reductive amination conditions N-[2-(3,4-dichlorophenyl)-4-oxobutyl]-N-[(2-carboxyethyl)ethyl]-3-cyano-1-naphthamide (0.256 g) was reacted with 4-(4-methoxy-2-(S)-methylsulfinylphenyl)piperidine (0.131 g) (synthesis described in a previous filing) to afford 0.297 g of product after purification by chromatography (100:1→20:1, DCM:MeOH w/0.5% conc. NH$_{3(aq)}$); MS: m/z 748 (M+); $^1$H NMR (CDCl$_3$) δ 8.26–8.20 (m), 7.98–7.20 (m), 7.03–6.53 (m), 4.55 (t), 4.11–2.20 (m), 3.87 (s), 2.68 (s), 2.65 (s), 2.10–1.50 (m), 1.33 (t), 1.20 (t).

Example 38

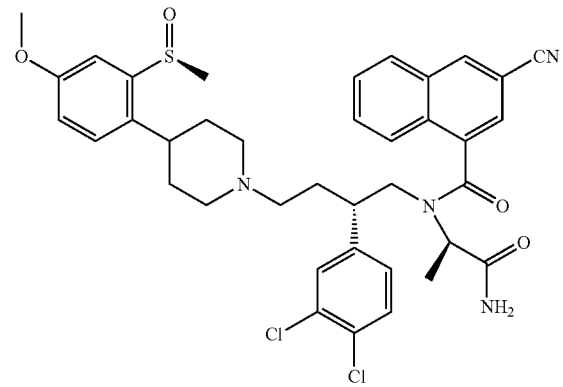

N-[2-(3,4-Dichlorophenyl)-4-[4-[4-methoxy-(S)-2-methylsulfylphenyl]-1-piperidinyl]-butyl]-N-[(1-(R)-carboxamide)ethyl]-3-cyano-1-naphthamide citrate N-[2-(3,4-Dichlorophenyl)-4-[4-[4-methoxy-(S)-2-methylsulfinylphenyl]-1-piperidinyl]butyl]-N-[(1-(R)-carboxymethyl)ethyl]-3-cyano-1-naphthamide was dissolved in 12 mL MeOH (2.0 M in NH$_3$) and heated to 70° C. in a sealed tube for 20 h. Mixture was cooled, MeOH was evaporated, product was purified by chromatography (100:1→20:1, DCM:MeOH w/0.5% conc. NH$_{3(aq)}$) and converted to the citrate salt; MS: m/z 719 (M+); $^1$H NMR (DMSO-d$_6$) δ 8.67 (s), 8.62 (s), 8.30–7.98 (m), 7.90–6.61 (m), 3.82 (s), 4.50–1.20 (m), 0.73 (d).

Intermediates were prepared as follows:

[2-(3,4-Dichlorophenyl)]-N-[(1-(R)-carboxymethyl)ethyl]-4-pentenanidne

D-Alanine methyl ester hydrochloride (0.73 g) was stirred with 30 mL MeOH and 0.75 mL Et$_3$N until all had dissolved. To this was added (1.15 g) 4-[2-(3,4-dichlorophenyl)]-pentenal followed by 1.45 mL HOAc. Mixture was stirred for 1.5 h, 0.50 g of NaCNBH$_3$ was added, and mixture was stirred for 18 h. At this point 50 mL of 20% K$_2$CO$_{3\,(aq)}$ was added, MeOH was evaporated, and aqueous residue was extracted with DCM. Extracts were dried over Na$_2$SO$_4$, filtered, and concentrated to give an oil (1.53 g); MS: m/z 316 (M+).

N-[2-(3,4-Dichlorophenyl)-4-pentenyl]-N-[(1-(R)-carboxymethyl)ethyl]-3-cyano-1-naphthamide 1-Naphthoyl chloride (1.07 g) was combined with [2-(3,4-dichlorophenyl)]-N-[(1-(R)-carboxymethyl)ethyl]-4-pentenamine (1.53 g) and triethyl amine under standard acylation conditions to afford N-[2-(3,4-dichlorophenyl)-4-pentenyl]-N-[(1-(R)-carboxymethyl)ethyl]-3-cyano-1-naphthamide (1.05 g) as a solid after purification by chromatography (5:4:1 Hexane:DCM:EtOAc); MS: m/z 495 (M+); $^1$H NMR (CDCl$_3$) δ 8.37–8.11 (m), 7.99–6.40 (m), 5.85–5.55 (m), 5.54–5.21 (m), 5.20–4.69 (m), 4.38–2.41 (m), 2.25–1.81 (m), 1.79–0.75 (m).

N-[2-(3,4-Dichlorophenyl)-4-oxobutyl]-N-[(1-(R)-carboxymethyl)ethyl]-3-cyano-1-naphthamide To a stirred slurry of N-[2-(3,4-dichlorophenyl)-4-pentenyl]-N-[(1-(R)-carboxymethyl)ethyl]-3-cyano-1-naphthamide (1.05 g) and NaIO$_4$ (1.01 g) in 60 mL 1:1

THF:H₂O was slowly added 0.64 mL OsO₄ solution (4% w/w in H₂O). Mixture was stirred for 18 h, 10 mL sat'd Na₂S₂O₃(aq) was added, THF was evaporated, and aqueous residue was extracted with DCM. Extracts were dried over Na₂SO₄, filtered, and concentrated.

This gave 0.64 g of N-[2-(3,4-dichlorophenyl)-4-oxobutyl]-N-[(1-(R)-carboxymethyl)ethyl]-3-cyano-1-naphthamide after purification by chromatography (5:4:1 Hexane:DCM:EtOAc); MS: m/z 497 (M+); ¹H NMR (CDCl₃) δ 9.77 (s), 9.63 (s), 9.59 (s), 9.51 (s), 8.19–8.09 (m), 8.03–6.38 (m), 4.58–2.35 (m), 1.82 (q), 1.71 (d), 1.50 (d), 1.44 (d), 1.15 (d), 1.01 (d).

N-[2-(3,4-Dichlorophenyl)-4-[4-[4-methoxy-(S)-2-methylsulfinylphenyl]-1-piperidinyl]-butyl]-N-[(1-(R)-carboxymethyl)ethyl]-3-cyano-1-naphthamide Using standard reductive amination conditions N-[2-(3,4-dichlorophenyl)-4-oxobutyl]-N-[(1-(R)-carboxymethyl)ethyl]-3-cyano-1-naphthamide (0.644 g) was reacted with 4-(4-methoxy-2-(S)-methylsulfinylphenyl)piperidine (0.333 g) (synthesis described in a previous filing) to afford 0.621 g of product after purification by chromatography (100:1→20:1, DCM:MeOH w/0.5% conc. NH₃(aq)); MS: m/z 734 (M+); ¹H NMR (CDCl₃) δ 8.30–8.10 (m), 7.98–7.15 (m), 7.05–6.70 (m), 6.55–6.40 (m), 4.55–2.45 (m), 3.92 (s), 3.87 (s), 2.68 (s), 2.66 (s), 2.35–1.30 (m), 0.83 (dd).

Example 39

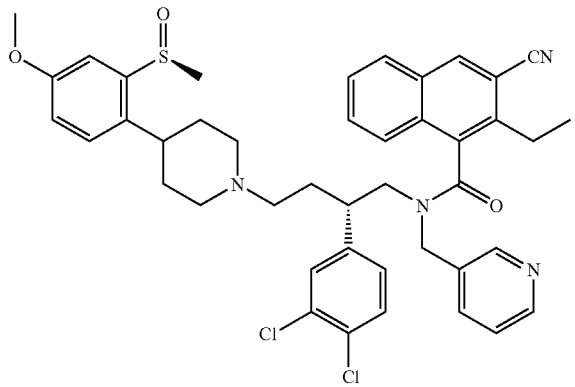

N-[2-(S)-(3,4-Dichlorophenyl)-4-[4-[4-methoxy-(S)-2-methylsulfinylphenyl]-1-piperidinyl]butyl]-N-[(3-pyridyl)methyl]-3-cyano-2-ethyl-1-naphthamide citrate Using standard reductive amination conditions 2-(S)-(3,4-dichlorophenyl)-4-[4-(4-methoxy-(S)-2-methylsulfinylphenyl)-1-piperidinyl]butanamine (0.244 g) (synthesis described in a previous filing) was reacted with 3-pyridine carboxaldehyde (0.055 g) to afford 0.267 g of N-[2-(S)-(3,4-dichlorophenyl)-4-[4-methoxy-(S)-2-methylsulfinylphenyl)-1-piperidinyl]]-N-[(3-pyridyl)methyl]butanamine which was used in the next step without purification; LC/MS indicated a single component: m/z 560 (M+). 3-Cyano-2-ethyl-1-naphthoyl chloride (0.129 g) (synthesis described in a previous fling) was combined with N-[2-(S)-(3,4-dichlorophenyl)-4-[4-(4-methoxy-(S)-2-methylsulfmylphenyl)-1-piperidinyl]]-N-[(3-pyridyl)methyl]butanamine (0.267 g) and triethyl amine under standard acylation conditions to afford 0.077 g of product after purification by chromatography and conversion to the citrate salt; MS: m/z 767 (M+); ¹H NMR (DMSO-d₆) δ 8.85–8.35 (m), 8.20–6.50 (m), 3.82 (s), 4.40–2.30 (m), 2.05–1.50 (m), 1.35–0.88 (m).

Example 40

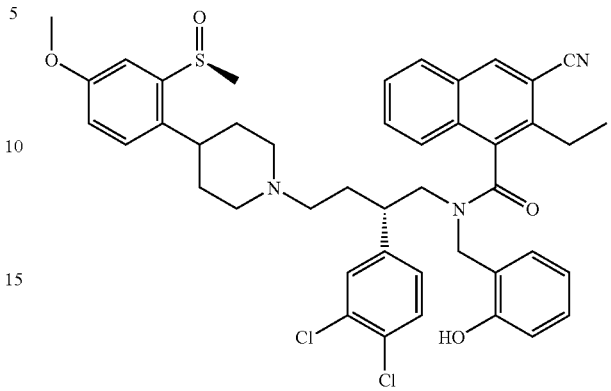

N-[2-(S)-(3,4Dichlorophenyl)-4-[4-[4-methoxy-(S)-2-methylsulfinylphenyl]-1-piperidinyl]butyl]-N-[2-hydroxyphenylmethyl]-3-cyano-2-ethyl-1-naphthamide citrate Using standard reductive amination conditions 2-(S)-(3,4-Dichlorophenyl)-4-[4-(4-methoxy-(S)-2-methylsulfinylphenyl)-1-piperidinyl]butanamine (0.244 g) (synthesis described in a previous filing) was reacted with salicylaldehyde (0.062 g) to afford 0.299 g of N-[2-(S)-(3,4-dichlorophenyl)-4-[4-(4-methoxy-(S)-2-methylsulfinylphenyl)-1-piperidinyl]]-N-[2-hydroxyphenylmethyl]butanamine (0.299 g) and triethyl amine under standard acylation conditions. Crude product after work-up was a mixture of O and N acylated material which was dissolved in 10 mL 1:1 THF:H₂O, mixed with 0.05 g LiOH, and stirred for 18 h. Reaction was quenched with 1 mL 1N HCl followed by 20 mL sat'd NaHCO₃. Result was extracted with DCM, extracts were dried over Na₂SO₄, filtered, and concentrated to afford 0.081 g of product after purification by chromatography and conversion to the citrate salt; MS: m/z 782 (M+); ¹H NMR (DMSO-d₆) 67 9.92–9.85 (m), 9.55–9.45 (m), 8.63–8.52 (m), 8.22–7.90 (m), 7.85–6.80 (m), 6.78–6.57 (m), 5.11 (d), 4.98 (d), 4.76 (t), 4.55 (t), 4.28 (t), 4.13 (d), 4.03 (d), 3.85 (s), 3.82 (s), 3.65–1.42 (m), 1.41–0.78 (m).

Example 41

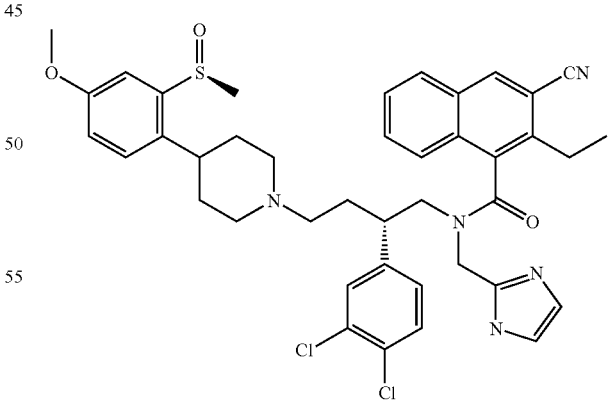

N-[2-(S)-(3,4-Dichlorophenyl)-4-[4-[4-methoxy-(S)-2-methylsulfmylpheny]-1-piperidinyl]butyl]-N-[(2-imidazoyl)methyl]-3-cyano-2-ethyl-1-naphthamide citrate Using standard reductive amination conditions 2-(S)-(3,4-Dichlorophenyl)-4-[4-(4-methoxy-(S)-2- methylsulfinylphenyl)-1-piperidinyl]butanamine (0.244 g) (synthesis described in a previous filing) was reacted with 2-imidazole carboxaldehyde (0.051 g) to afford 0.286 g of N-[2-(S)-(3,4-dichlorophenyl)-4-[4-(4-methoxy-(S)-2-methylsulfinylphenyl)-1-piperidinyl]]-N-[(2-imidazoyl)methyl]butanamine which was used in the next step without purification; LC/MS indicated a major component: m/z 549 (M+). 3-Cyano-2-ethyl-1-naphthoyl chloride (0.129 g) (synthesis described in a previous filing) was combined with N-[2-(S)-(3,4-dichlorophenyl)-4-[4-(4-methoxy-(S)-2-methylsulfinylphenyl)-1-piperidinyl]]-N-[(3-pyridyl)methyl]butanamine (0.286 g) and triethyl amine under standard acylation conditions to afford 0.108 g of product after purification by chromatography and conversion to the citrate salt; MS: m/z 756 (M+); $^1$H NMR (DMSO-d$_6$) δ 11.18 (br m), 8.90 (s), 8.64 (s), 8.60 (s), 8.25–8.00 (m), 7.97 (d), 7.85–6.90 (m), 6.73 (d), 6.64 (s), 6.44 (s), 6.38 (d), 4.99 (d), 4.90 (d), 4.69 (d), 4.62 (d), 3.82 (s), 3.81 (s), 4.18–1.40 (m), 1.30–0.89 (m).

Example 42

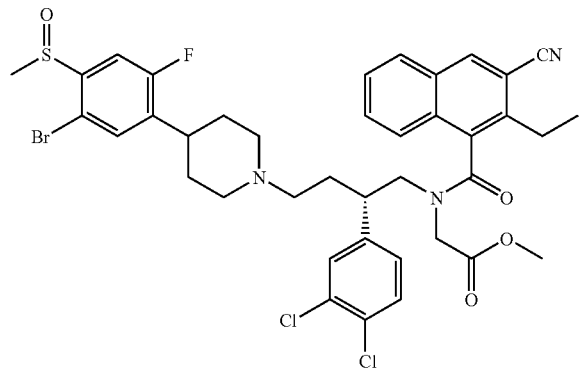

N-[2-(S)-(3,4-Dichlorophenyl)-4-[4-(5-bromo-2-fluoro-4-(R,S)-methylsulfinylphenyl)-1-piperidinyl]butyl-N-[(carboxymethyl)methyl]-3-cyano-1-naphthamide citrate Using standard reductive amination conditions N-[2-(S)-(3,4-dichlorophenyl)-4-oxobutyl]-N-[(carboxymethyl)methyl]-3-cyano-1-naphthamide (0.478 g) (synthesis described elsewhere in this patent) was reacted with 4-(5-bromo-2-fluoro-4-(R,S)-methylsulfmylphenyl)piperidine (0.322 g) to afford 0.780 g of N-[2-(S)-(3,4-dichlorophenyl)-4-[4-(5-bromo-2-fluoro-4-(R,S)-methylsulfinylphenyl)-1-piperidinyl]butyl-N-[(carboxymethyl)methyl]-3-cyano-1-naphthamide after purification by chromatography (50:1→20:1, DCM:MeOH w/0.5% conc. NH$_{3(aq)}$; MS: m/z 788 (M+); $^1$H NMR (CDCl$_3$) δ 8.32–8.14 (m), 8.07–6.60 (m), 4.73 (d), 4.60–4.20 (m), 4.09–2.61 (m), 2.82 (s), 2.81 (s), 2.40–2.21 (m), 2.15–1.30 (m). N-[2-(S)-(3,4-Dichlorophenyl)-4-[4-(5-bromo-2-fluoro-4-(R,S)-methylsulfinylphenyl)-1-piperidinyl]butyl-N-[(carboxymethyl)methyl]-3-cyano-1-naphthamide citrate; MS: m/z 788 (M+); $^1$H NMR (DMSO-d$_6$) δ 8.86–8.59 (m), 8.22 (d), 8.15 (d), 8.09 (d), 7.90–7.35 (m), 7.28 (d), 7.17 (d), 7.04 (d), 6.95 (d), 6.54 (d), 6.46 (s), 4.61 (d), 4.50–1.50 (m), 3.80 (s), 3.77 (s), 2.81 (s).

Example 43

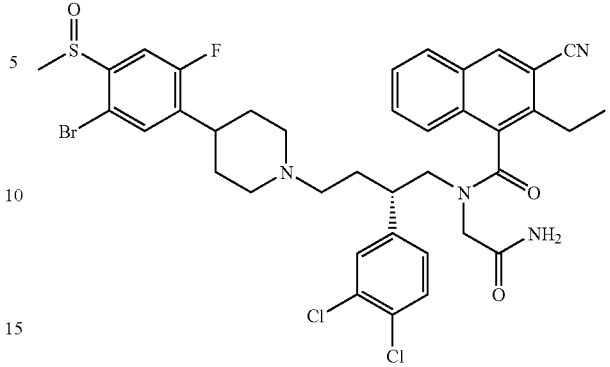

N-[2-(S)-(3,4-Dichlorophenyl)-4-[4-(5-bromo-2-fluoro-4-(R,S)-methylsulfinylphenyl)-1-piperidinyl]butyl-N-[(carboxamiide)methyl]-3cyano-1-naphthamide citrate N-[2-(S)-(3,4-Dichlorophenyl)-4-[4-(5-bromo-2-fluoro-4-(R,S)-methylsulfinylphenyl)-1-piperidinyl]butyl-N-[(carboxymethyl)methyl]-3-cyano-1-naphthamide (0.780 g) was dissolved in 12 mL MeOH (2.0 M in NH$_3$) and heated to 70° C. in a sealed tube for 20 h. Mixture was cooled, MeOH was evaporated, product was purified by chromatography (100:1→20:1, DCM:MeOH w/0.5% conc. NH$_{3(aq)}$) and converted to the citrate salt (0.200 g); MS: m/z 773 (M+); $^1$H NMR (DMSO-d$_6$) δ 8.70–8.57 (m), 8.43 (d), 8.19–7.99 (m), 7.94 (s), 7.85–6.91 (m), 6.55 (s), 6.47 (d), 4.62–1.40 (m), 2.81 (s), 2.80 (s).

The intermediates were prepared as follows:

4-Hydroxy-4-(4-fluoro-2-methylthiophenyl)-N-Cbz-piperidine and 4-Hydroxy-4-(5-bromo-2-fluoro-4-methylthiophenyl)-N-Cbz-piperidine Cerium (III) chloride heptahydrate (246.8 g) was heated under high vacuum at 100° C. for 2 days then at 140° C. for two days. This material was transferred to a dry flask equipped with mechanical stirrer, suspended in 1200 mL anhydrous THF, and stirred while cooling to −78° C. A solution of 2-bromo-5-fluoro-(thiomethyl)benzene (130.2 g) in 1200 mL anhydrous THF was cooled to −78° C. and treated dropwise with n-butyllithium (236.0 mL of a 2.5 M solution in hexane) over 1 hour. The temperature of the reaction flask was kept below −70° C. during the addition. This mixture was stirred at −78° C. for 1.5 hours and transferred via wide bore insulated cannula into the flask containing the stirred suspension of CeCl$_3$ at −78° C. The resulting yellow suspension was stirred for 1 h at −78° C. and then a solution of 1-benzyloxycarbonyl-4-piperidone (137.4 g in 200 mL anhydrous THF) was added via cannula over 30 minutes. When the addition was complete the reaction mixture was warmed to room temperature and stirred overnight (18 h). At the end of this period the reaction mixture was quenched with 800 mL saturated NH$_4$Cl (4 scoops of celite was added) and stirred for 30 minutes. The organic layer was decanted, concentrated under reduced pressure, and set aside. The remaining grayish suspension was filtered and cake was washed with EtOAc (4×75 mL). The EtOAc washings and the THF concentrate were combined, dried over MgSO$_4$, filtered, and concentrated under reduced pressure to give a viscous oil which was purified by chromatography on silica (2 kg)

(9:1→8:2→7:3→1:1, EtOAc:hexane) to give 96.00 g of pure 4-hydroxy-4-(4-fluoro-2-methylthiophenyl)-N-Cbz-piperidine; MS m/z 358 (M-H₂O). ¹H NMR (CDCl₃) δ 7.45–7.25 (m), 7.08 (dd), 6.95–6.80 (m), 5.15 (s), 4.30–4.00 (m), 3.82 (s), 3.45–3.20 (m), 2.52 (s), 2.25–1.95 (m). As a side product 4-hydroxy-4-(5-bromo-2-fluoro-4-methylthiophenyl)-N-Cbz-piperidine was also isolated; MS m/z 436 (M-H₂O); ¹H NMR (CDCl₃) δ 7.65 (d), 7.41–7.29 (m), 6.80 (d), 5.15 (s), 4.30–4.00 (m), 3.47–3.20 (m), 2.45 (s), 2.25–1.90 (m), 1.74 (d).

4-(5-Bromo-2-fluoro-4-methylthiophenyl)-N-Cbz-piperidine

To an ice-cooled, rapidly stirred slurry of 4-hydroxy-4-(5-bromo-2-fluoro-4-methylthiophenyl)-N-Cbz-piperidine (7.82 g) in triethylsilane (19.7 g) was slowly added trifluoroacetic acid (18.6 g). When addition was complete the mixture was warmed to room temperature and stirred overnight (18 h). At the end of this period the mixture was poured into 100 mL saturated NaHCO₃ and extracted with DCM. Extracts were combined, dried over Na₂SO₄, filtered, and concentrated under reduced pressure to give an oil. The product was purified by chromatography on silica (7:3, hexane:EtOAc) to give 5.18 g of an oil; MS m/z 438 (M+); ¹H NMR (CDCl₃) δ 7.45–7.30 (m), 7.25 (d), 6.80 (d), 5.15 (s), 4.50–4.20 (m), 3.11–2.80 (m), 1.90–1.48 (m).

4-5-Bromo-2-fluoro-4-(R,S)-methylsulfinylphenyl)-N-Cbz-pipexidine

To a stirred solution of NaIO₄ (10.93 g) dissolved in 100 mL H₂O was added 4-(5-bromo-2-fluoro-4-methylthiophenyl)-N-Cbz-piperidine (4.25 g) dissolved in 100 mL THF. Mixture was stirred at room temperature for 18 h, 50 mL sat'd NaHCO₃ was added, and THF was evaporated. Result was extracted with DCM (3×75 mL), extracts were combined, dried over Na₂SO₄, and evaporated to give 2.51 g of product after chromatography (1:1 hexane:EtOAc); MS m/z 454 (M+); ¹H NMR (CDCl₃) δ 7.65 (d), 7.45–7.25 (m), 5.16 (s), 4.53–4.25 (m), 3.07 (tt), 3.00–2.75 (m), 2.82 (s), 1.85 (d), 1.75–1.56 (m).

4-(5-Bromo-2-fluoro-4-(R,S)-methylsulfinylphenyl)piperidine

A solution of TFA (10 mL) and 2.344 g 4-(5-bromo-2-fluoro-4-(R,S)-methylsulfinylphenyl)-N-Cbz-piperidine was heated to 80° C. for 2 h. TFA was evaporated, residue was mixed with 30 mL 20% KOH₍ₐq₎, and extracted with CHCl₃. Extracts were combined, dried over Na₂SO₄, and evaporated. Reside was purified by chromatography (50:1→10:1, DCM:MeOH w/0.5% conc. NH₃₍ₐq₎) to give 0.425 g product; MS m/z 320 (M+); ¹H NMR (CDCl₃) δ 7.63 (d), 7.43 (d), 3.21 (dm), 3.01 (tt), 2.82 (s), 2.78 (tm), 1.83 (dm), 1.75–1.57 (m).

Example 44

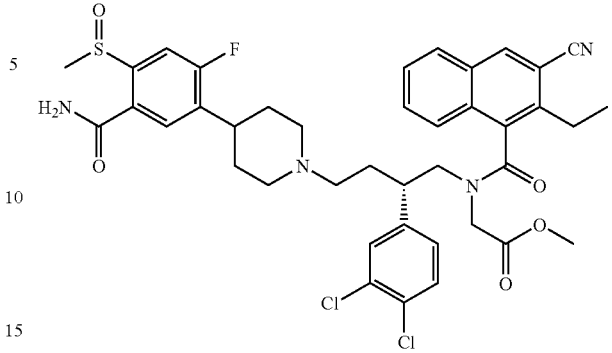

N-[2-(S)-(3,4-Dichlorophenyl)-4-[4-5-carboxamide-2-fluoro-4-(R,S)-methylsulinylphenyl)-1-piperidinyl]butyl-N-[(carboxymethyl)methyl]-3-cyano-1-naphthamide citrate Using standard reductive amination conditions N-[2-(S)-(3,4-dichlorophenyl)-4-oxobutyl]-N-[(carboxymethyl) methyl]-3-cyano-1-naphthamide (0.343 g) (synthesis described elsewhere in this patent) was reacted with 4-(5-carboxamide-2-fluoro-4-(R,S)-methylsulfinylphenyl) piperidine (0.197 g) to afford 0.351 g of N-[2-(S)-(3,4-dichlorophenyl)-4-[4-(5-carboxamide-2-fluoro-4-(R,S)-methylsulfinylphenyl)-1-piperidinyl]butyl-N-[(carboxymethyl)methyl]-3-cyano-1-naphthamide after purification by chromatography (50:1→20:1, DCM:MeOH w/0.5% conc. NH₃₍ₐq₎); MS: m/z 751 (M+); ¹H NMR (CDCl₃) δ 8.38–6.55 (m), 5.57 (br s), 4.94 (t), 4.59 (d), 4.05–1.15 (m). N-[2-(S)-(3,4-Dichlorophenyl)-4-[4-(5-carboxamide-2-fluoro-4-(R,S)-methylsulfinylphenyl)-1-piperidinyl]butyl-N-[(carboxymethyl)methyl]-3-cyano-1-naphthamide citrate; MS: m/z 751 (M+); ¹H NMR (DMSO-d₆) δ 8.87–8.59 (m), 8.42–8.30 (m), 8.22 (d), 8.15 (d), 8.09 (d), 7.90–7.35 (m), 7.27 (d), 7.17 (d), 7.04 (d), 6.94 (d), 6.54 (d), 6.44 (s), 4.61 (d), 4.50–1.50 (m), 3.80 (s), 3.77 (s), 2.77 (s), 2.76 (s).

Example 45

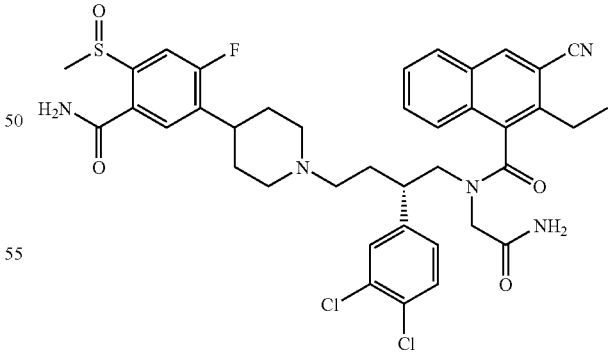

N-[2-(S)-(3,4-Dichlorophenyl)-4-[4-(5-carboxamide-2-fluoro-4-(R,S)-methylsulfinylphenyl)-1-piperidinyl]butyl-N-[(carboxamide)methyl]-3-cyano-1-naphthamide citrate N-[2-(S)-(3,4-Dichlorophenyl)-4-[4-(5-carboxamide-2-fluoro-4-(R,S)-methylsulfinylphenyl)-1-piperidinyl]butyl- N-[(carboxymethyl)methyl]-3-cyano-1-naphthamide (0.351 g) was dissolved in 12 mL MeOH (2.0 M in $NH_3$) and heated to 80° C. in a sealed tube for 18 h. Mixture was cooled, MeOH was evaporated, product was purified by chromatography (100:1→20:1, DCM:MeOH w/0.5% conc. $NH_{3(aq)}$) and converted to the citrate salt (0.148 g); MS: m/z 736 (M+); $^1$H NMR (DMSO-$d_6$) δ 8.70–8.58 (m), 8.50–8.29 (m), 8.19–8.01 (m), 7.99–6.97 (m), 6.58–6.42 (m), 4.62–1.48 (m), 2.77 (s), 2.76 (s).

The intermediates were prepared as follows:

4-(2-Fluoro-4-methylthio-5-methoxycarbonylphenyl)-N-Cbz-piperidine

To a mixture of DMSO (90 mL) and MeOH (90 mL) was added 1,3-bis(diphenylphosphino)propane (1.02 g), $Pd(OAc)_2$ (0.561 g), 4-5-bromo-2-fluoro-4-methylthiophenyl)-N-Cbz-piperidine (5.18 g), and 2.5 mL $Et_3N$. Mixture was purged with CO (via 18 ga. needle and balloon) for 30 minutes and heated to 70° C. Mixture was kept under CO atmosphere (atmosphereic pressure) for 18 h at 70° C. At this time mixture was poured into 500 mL of 1:1 EtOAc:hexane, extracted with $H_2O$ (6×150 mL), dried over $MgSO_4$, filtered, and concentrated. Residue was purified by chromatography (5:4.5:0.5, hexane:DCM:EtOAc) to give 1.38 g of product; MS m/z 418 (M+); $^1$H NMR ($CDCl_3$) δ 7.89 (d), 7.45–7.25 (m), 6.92 (d), 5.16 (s), 4.50–4.21 (m), 3.90 (s), 2.99 (tt), 3.01–2.78 (m), 2.43 (s), 1.82 (dm), 1.79–1.51 (m).

4-(2-Fluoro-4-methylthio-5-carboxyphenyl)-N-Cbz-piperidine

To a solution of 4-(2-fluoro-4-methylthio-5-methoxycarbonylphenyl)-N-Cbz-piperidine (1.38 g) dissolved in 100 mL 1:1 THF:$H_2O$ was added 0.45 g LiOH. Mixture was stirred for 18 h, THF was evaporated, residue was mixed with 25 mL 1N HCl, and extracted with DCM (3×50 mL). Extracts were combined, dried over $Na_2SO_4$, and evaporated to give 1.33 g product; MS m/z 404 (M+H); $^1$H NMR ($CDCl_3$) δ 8.01 (d), 7.45–7.25 (m), 6.94 (d), 5.17 (s), 4.50–4.21 (m), 2.99 (tt), 3.01–2.78 (m), 2.44 (s), 1.84 (dm), 1.69 (qd).

4-(5-Carboxamide-2-fluoro-4-methylthiophenyl)-N-Cbz-piperidine

To a solution of 4-(2-fluoro-5-methylthio-5-carboxyphenyl)-N-Cbz-piperidine (1.33 g) dissolved in 60 mL DCM was added 1.6 mL of N,N-diisopropylethylamine. Mixture was stirred for 10 min and then 1.15 g tetramethylfluoroformamidiniuiiihexafluorophosphate was added and stirring was continued for 1 h. At this point 1.05 g HOBt·$PNH_3$ was added and the solution was stirred overnight. Then 20 mL of sat'd $NaHCO_3$ was added and the result was extracted with DCM to give a solid (1.12 g) after purification by chromatography (20:1 DCM:MeOH); MS m/z 403 (M+H); $^1$H NMR ($CDCl_3$) δ 7.57 (d), 7.48–7.27 (m), 6.99 (d), 6.46 (br s), 5.86 (br s), 5.15 (s), 4.51–4.21 (m), 2.99 (tt), 3.01–2.75 (m), 2.47 (s), 181 (dm), 1.68 (qd). HOBt.$NH_3$ was prepared using the procedure of Bajusz et. al. as described in *FEBS Letters*, 1977, 76, 91–92.

4-(5-Carboxamide-2-fluoro-4-(R,S)-methylsulfinylphenyl)-N-Cbz-piperidine

To a stirred solution of $NaIO_4$ (4.30 g) dissolved in 70 mL $H_2O$ was added 4-(5-carboxamide-2-fluoro-4-methylthiophenyl)-N-Cbz-piperidine (1.12 g) dissolved in 70 mL THF. Mixture was stirred at room temperature for 18 h, 50 mL sat'd $NaHCO_3$ was added and THF was evaporated. Result was extracted with DCM (3×75 mL). Organic extracts were combined, dried over $Na_2SO_4$, and evaporated to give 1.12 g of product after chromatography (20:1 DCM:MeOH); MS m/z 419 (M+H); $^1$H NMR ($CDCl_3$) δ 7.98 (d), 7.52 (d), 7.43–7.25 (m), 6.39 (br s), 5.66 (br s), 5.15 (s), 4.50–4.22 (m), 3.14 (tt), 3.05–2.82 (m), 2.89 (s), 1.87 (dm), 1.80–1.52 (m).

4-(5-Carboxamide-2-fluoro-4-(R,S)-methylsulfinylphenyl)piperidine

A solution of TFA (5 mL) and 4-(5-carboxamide-2-fluoro-4-(R,S)-methylsulfinylphenyl)-N-Cbz-piperidine (0.560 g) was heated to 90° C. for 0.5 h. TFA was evaportated, residue was mixed with 30 mL 20% $KOH_{(aq)}$, and extracted with $CHCl_3$. Extracts were combined, dried over $Na_2SO_4$, and evaporated. Reside was purified by chromatography (50:1→10:1, DCM:MeOH w/1% conc. $NH_{3(aq)}$) to give 0.197 g product; MS m/z 285 (M+H); $^1$H NMR (DMSO-$d_6$) δ 8.37 (br s), 7.95 (d), 7.75 (d), 7.68 (br s), 3.06 (d) 3.01–2.40 (m), 2.76 (s), 1.69 (br m).

Example 46

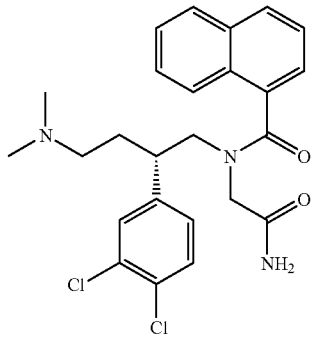

N-[2-(3,4-Dichlorophenyl)-4-(dimethylamino) butyl]-N-[(carboxamide)methyl]-1-naphthamide citrate Glycinamide hydrochloride (0.114 g) and 2-(3,4-dichlorophenyl)-4-(dimethyamino)-butanal (0.260 g) was stirred with 15 mL MeOH containing 0.15 mL $Et_3N$. When all had dissolved 0.30 mL HOAc was added and mixture was stirred for 1 h. At this time of $NaCNBH_3$ (0.100 g in 2 mL MeOH) was added and mixture was stirred for 18 h. At this point 30 mL of 20% $K_2CO_{3(aq)}$ was slowly added, MeOH was evaporated, and aqueous residue was extracted with DCM. Extracts were dried over $Na_2SO_4$, filtered, and concentrated to afford N-[2-(3,4-dichlorophenyl)-4-(dimethylamino)butyl]-N-[(carboxamide)methyl]-amine which was used in the next step without purification; MS: m/z 318 (M+). 1-Naphthoyl chloride (0.202 g) was combined with N-[2-(3,4-dichlorophenyl)-4-(dimethylamino) butyl]-N-[(carboxamide)methyl]-amine (0.318 g) and triethyl amine under standard acylation conditions to afford 0.253 g of product after purification by chromatography and conversion to the citrate salt; MS: m/z 472 (M+); $^1$H NMR (DMSO-$d_6$) δ 8.30–8.20 (m), 8.00–6.85 (m), 4.56 (t), 4.42 (d), 4.20–1.90 (m), 1.80–1.45 (m).

Example 47

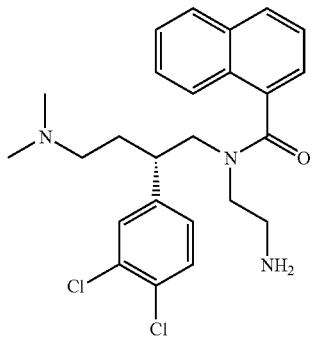

N-[2-(3,4-Dichlorophenyl)-4-(dimethylamino)butyl]-N-[2-aminoethyl]-1-naphthamide citrate A solution of TFA (3 mL) and N-[2-(3,4-dichlorophenyl)-4-(dimethylamino)butyl]-N-[N-boc-2-aminoethyl[-1-naphthamide (0.178 g) was stirred for 0.5 h. TFA was evaporated, residue was mixed with 30 mL 20% KOH$_{(aq)}$, and extracted with CHCl$_3$. Extracts were combined, dried over Na$_2$SO$_4$, and evaporated. Product was converted to the citrate salt; MS: m/z 458 (M+); $^1$H NMR (DMSO-d$_6$) δ 8.10–7.90 (m), 7.80–6.65 (m), 6.29 (d), 4.59 (t), 3.98–1.30 (m). From:

N-[2-(3,4-Dichlorophenyl)-4-(dimethylamino)butyl]-N-[N-boc-2-aminoethyl]-1-naphthamide Using standard reductive amination conditions 2-(3,4-dichlorophenyl)-4-(dimethyamino)-butanal (0.260 g) was reacted with tert-butyl N-(2-aminoethyl)-carbamate (0.166 g) to afford 0.404 g of product which was used in the next step without purification; MS: m/z 404 (M+). 1-Naphthoyl chloride (0.191 g) was combined with N-[2-(3,4-dichlorophenyl)-4-(dimethylamino)butyl]-N-[N-boc-2-aminoethyl]-amine (0.404 g) and triethyl amine under standard acylation conditions to afford 0.178 g of N-[2-(3,4-dichlorophenyl)-4-(dimethylamino)butyl]-N-[N-boc-2-aminoethyl]-1-naphthamide after purification by chromatography (100:1→50:1, DCM:MeOH w/0.1% conc. NH$_{3(aq)}$); MS: m/z 558 (M+); $^1$H NMR (CDCl$_3$) δ 7.92–7.70 (m), 7.65–6.98 (m), 6.86 (d), 6.84–6.67 (m), 6.57 (d), 5.20 (br s), 4.40–2.50 (m), 2.21 (s), 2.03 (s), 2.00 (s), 1.48 (s), 1.41 (s), 2.40–1.20 (m).

Example 48

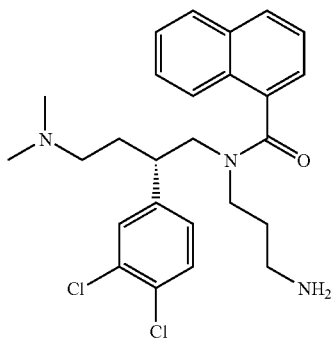

N-[2-(3,4-Dichlorophenyl)-4-(dimethylamino)butyl]-N-[3-aminopropyl]-1-naphthamide citrate A solution of TFA (3 mL) and N-[2-(3,4-dichlorophenyl)-4-(dimethylamino)butyl]-N-[N-boc-3-aminopropyl]-1-naphthamide (0.217 g) was stirred for 0.5 h. TFA was evaporated, residue was mixed with 30 mL 20% KOH$_{(aq)}$, and extracted with CHCl$_3$. Extracts were combined, dried over Na$_2$SO$_4$, and evaporated. Product was converted to the citrate salt; MS: m/z 472 (M+); $^1$H NMR (DMSO-d$_6$) δ 8.10–7.90 (m), 7.80–7.00 (m), 6.95 (d), 6.75 (d), 6.58 (d), 6.27 (d), 4.59 (t), 3.89–1.31 (m). From:

N-[2-(3,4-Dichlorophenyl)-4-(dimethylamino)butyl]-N-[N-boc-3-aminopropyl]-1-naphthamide Using standard reductive amination conditions 2-(3,4-dichlorophenyl)-4-(dimethyamino)-butanal (0.260 g) was reacted with tert-butyl N-(3-aminopropyl)-carbamate (0.180 g) to afford 0.418 g of product which was used in the next step without purification; MS: m/z 418 (M+). 1-Naphthoyl chloride (0.191 g) was combined with N-[2-(3,4-dichlorophenyl)-4-(dimethylamino)butyl]-N-[N-boc-3-aminopropyl]-amine (0.418 g) and triethyl amine under standard acylation conditions to afford 0.217 g of N-[2-(3,4-dichlorophenyl)-4-(dimethylamino)butyl]-N-[N-boc-3-aminopropyl]-1-naphthamide after purification by chromatography (100:1→50:1, DCM:MeOH w/0.1% conc. NH$_{3(aq)}$); MS: m/z 572 (M+); $^1$H NMR (CDCl$_3$) δ 7.92–7.67 (m), 7.66–6.96 (m), 6.84 (d), 6.80–6.64 (m), 6.51 (d), 5.30 (br s), 4.39 (t), 4.21–2.40 (m), 2.21 (s), 2.04 (s), 1.99 (s), 1.45 (s), 1.34 (s), 2.35–1.20 (m).

The intermediates were prepared as follows:

5-(tert-Butyldimethylsilyloxy)-4-(3,4-dichlorophenyl)-1-pentene

To a stirred solution of 4-[2-(3,4-dichlorophenyl)]-pentenol (23.93 g) in 500 mL DCM was added Et$_3$N (23.0 mL) and 4-dimethylaminopyridine (6.18 g). When all had dissolved tert-butyldimethylsilyl chloride (22.90 g) was added, reaction was stirred for 3 h, quenched with 100 mL sat'd NaCO$_3$, and DCM was evaporated. Aqueous mixture was extracted with EtOAc (3×120 mL). Organic extracts were combined and washed with 1N HCl (3×120 mL), sat'd NaHCO$_3$ (100 mL), and brine (100 mL). EtOAc layer was dried over MgSO$_4$, filtered, and concentrated to give an oil (31.34 g); $^1$H NMR (CDCl$_3$) δ 7.37 (d), 7.33 (d), 7.06 (dd), 5.69 (ddt), 5.17–4.88 (m), 3.70 (d), 2.79 (tt), 2.57 (dt), 2.33 (dt), 0.87 (s), −0.03 (s).

5-(tert-Butyldimethylsilyloxy)-3-(3,4-dichlorophenyl)-1-butanal

To a stirred slurry 5-(tert-butyldimethylsilyloxy)-4-(3,4-dichlorophenyl)-1-pentene (34.31 g) and NaIO$_4$ (46.01 g) in 900 mL 1:1 THF:H$_2$O was slowly added 30 mL OsO$_4$ solution (4% w/w in H$_2$O). Mixture was stirred for 30 h, 200 mL sat'd Na$_2$S$_2$O$_{3(aq)}$ was added, mixture was stirred for 15 minutes, and filtered (cake was washed with THF (3×50 mL)). THF was evaporated, and aqueous residue was mixed with 500 mL 1:1 hexane:EtOAc. Organic layer was washed with sat'd Na$_2$S$_2$O$_{3(aq)}$ (150 mL), sat'd NaHCO$_3$ (200 mL), and brine (200 mL). Extract was dried over MgSO$_4$, filtered, and concentrated. Product was purified by chromatography (9:1, hexane:EtOAc) to give 16.4 g of an oil; $^1$H NMR (CDCl$_3$) δ 9.76 (m), 7.39 (d), 7.36 (d), 7.09 (dd), 3.76 (dd), 3.63 (dd), 3.39 (dt), 2.96 (ddd), 2.73 (ddd), 0.88 (s), 0.02 (s).

N-[5tert-Butyldimethylsilyloxy)-3-(3,4-dichlorophenyl)butyl]-dimethylamine

Dimethylamine hydrochloride (4.11 g) and 5-(tert-butyldimethylsilyloxy)-3-(3,4-dichlorophenyl)-1-butanal (16.40 g) was stirred with 300 mL MeOH containing 7.80 mL Et₃N. When all had dissolved 14.5 mL HOAc was added and mixture was stirred (pH 4) was stirred for 1.5 h. At this time of NaCNBH₃ (4.94 g in 75 mL MeOH) was added via cannula and mixture was stirred for 3 h. At this point 200 mL of 20% $K_2CO_{3(aq)}$ was slowly added, MeOH was evaporated, and aqueous residue was extracted with DCM. Extracts were dried over Na₂SO₄, filtered, and concentrated to give an oil (17.75 g); MS: m/z 376 (M+); ¹H NMR (CDCl₃) δ 7.38 (d), 7.34 (d), 7.08 (dd), 3.68 (d), 2.78 (dq), 2.24 (s), 2.32–2.10 (m), 2.09–1.95 (m), 1.73 (dtd), 0.87 (s), −0.02 (s), −0.03 (s).

2-(3,4-Dichlorophenyl)-4-(dimethyamino)-butanol

To a stirred solution of N-[5-(tert-butyldimethylsilyloxy)-3-(3,4-dichlorophenyl)butyl]-dimethylamine (17.75 g) in 100 mL THF was added tetrabutylammonium fluoride (70 mL of 1.0M in THF). Mixture was stirred for 3 h, THF was evaporated, residue was mixed with 150 mL 2 N KOH (with cooling), and extracted with CHCl₃. Extracts were dried over Na₂SO₄, filtered, and concentrated to give an oil which was purified by chromatography (50:1→10:1, DCM:MeOH w/1.0% conc. $NH_{3(aq)}$) to afford 7.00 g product which was contaminated with tetrabutyammonium hydroxide; MS: m/z 262 (M+); ¹H NMR (CDCl₃) δ 7.36 (d), 7.31 (d), 7.06 (dd), 3.78–3.58 (m), 2.90–2.72 (m), 2.52 (ddd), 2.42–2.20 (m), 2.33 (s), 2.08–1.78 (m).

2-(3,4-Dichlorophenyl)-4-(dimethyamino)-butanal 2-(3,4-Dichlorophenyl)-4-(dimethyamino)-butanol (1.40 g) was reacted with oxalyl chloride/DMSO under standard swern oxidizing conditions in DCM (80 mL) to afford (1.60 g crude) as a oil which was contaminated with tetrabutyammonium cation after aqueous extraction from DCM; MS: m/z 260 (M+); ¹H NMR (CDCl₃) δ 9.57 (d), 7.44 (d), 7.33 (d), 7.07 (dd), 3.66 (t), 2.35–2.03 (m), 2.22 (s).

Example 49

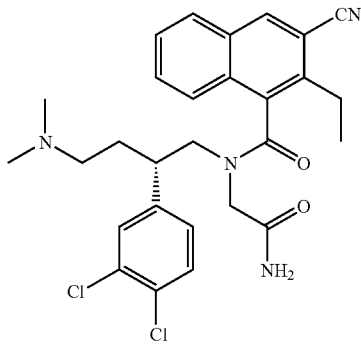

N-[2-(3,4-Dichlorophenyl)-4-dimethylamino]-N-[(carboxamide)methyl]-3-cyano-2-ethyl-1-naphthamide citrate N-[2-(3,4-Dichlorophenyl)-4-(dimethylarino)]-N-[(carboxymethyl)methyl]-3-cyano-2-ethyl-1-naphthamide (0.276 g) was dissolved in 12 mL MeOH (2.0 M in NH₃) and heated to 80° C. in a sealed tube for 48 h. Mixture was cooled, MeOH was evaporated, product was purified by chromatography (100:1→10:1, DCM:MeOH w/0.5% conc. $NH_{3(aq)}$ and converted to the citrate salt (0.160 g); MS: m/z 525 (M+); ¹H NMR (DMSO-d₆) δ 11.07 (br m), 8.71–8.59 (m), 8.33 (d), 8.10 (d), 8.08–7.92 (m), 7.90–6.80 (m), 7.02 (s), 6.86 (s), 6.77 (d), 6.43 (d), 4.52 (t), 4.40–3.80 (m), 3.75–1.35 (m), 1.25–0.88 (m).

The intermediates were prepared as follows:

N-[2-(3,4-Dichlorophenyl)-4-pentenylbutyl]-N-[(carboxymethyl)methyl]-3-cyano-2-ethyl-1-naphthamide 3-Cyano-2-ethyl-1-naphthoyl chloride (0.49 g) was combined with N-[2-(3,4-dichlorophenyl)-4-pentenylbutyl]-N-[(carboxymethyl)methyl]-amine (0.57 g) and triethyl amine under standard acylation conditions to afford N-[2-(3,4-dichlorophenyl)-4-pentenylbutyl]-N-[(carboxymethyl)methyl]-3-cyano-2-ethyl-1-naphthamide (0.51 g) as a solid after purification by chromatography (5:4:1 Hexane:DCM:EtOAc); MS: m/z 509 (M+); ¹H NMR (CDCl₃) δ 8.29 (s), 8.26 (s), 7.83 (d), 7.98–7.30 (m), 7.01 (d), 6.80 (s), 6.53 (d), 5.30–5.11 (m), 4.85–4.52 (m), 4.35–4.03 (m), 4.22 (s), 3.84 (s), 3.80 (s), 3.45 (dd), 3.32 (dd), 3.20–2.91 (m), 1.37 (t).

N-[2-(3,4-Dichlorophenyl)-4-oxobutyl]-N-[(carboxymethyl)methyl]-3-cyano-2-ethyl-1-naphthamide To a stirred slurry of N-[2-(3,4-dichlorophenyl)-4-pentenylbutyl]-N-[(carboxymethyl)methyl]-3-cyano-2-ethyl-1-naphthamide (0.51 g) and NaIO₄ (0.47 g) in 100 mL 1:1 THF:H₂O was slowly added 0.32 mL OsO₄ solution (4% w/w in H₂O). Mixture was stirred for 18 h, 10 mL sat'd $Na_2S_2O_{3(aq)}$ was added, THF was evaporated, and aqueous residue was extracted with DCM. Extracts were dried over Na₂SO₄, filtered, and concentrated. This gave 0.64 g of N-[2-(3,4-dichlorophenyl)-4-oxobutyl]-N-[(carboxymethyl)methyl]-3-cyano-1-naphthamide after purification by chromatography (100:1, DCM:MeOH); MS: m/z 511 (M+); ¹H NMR (CDCl₃) δ 9.53 (s), 8.25 (s), 7.79 (d), 7.70–7.20 (m), 6.89 (d), 6.73 (d), 6.48 (dd), 4.58–4.20 (m), 3.88 (s), 3.84 (s), 3.60–3.21 (m), 3.18–2.82 (m), 2.65–2.32 (m), 1.33 (t).

N-[2-(3,4-Dichlorophenyl)-4-(dinethylamino)]-N-[(carboxymethyl)methyl]-3-cyano-2-ethyl-1-naphthamide Dimethylamine hydrochloride (0.063 g) and N-[2-(3,4-dichlorophenyl)-4-oxobutyl]-N-[(carboxymethyl)methyl]-3-cyano-2-ethyl-1-naphthamide (0.380 g) was stirred with 10 mL MeOH containing 0.13 mL Et₃N. When all had dissolved 0.12 mL HOAc was added and mixture was stirred for 1.5 h. At this time of NaCNBH₃ (0.073 g in 2 mL MeOH) was added and mixture was stirred for 18 h. At this point 10 mL of 20% $K_2CO_{3(aq)}$ was slowly added, MeOH was evaporated, and aqueous residue was extracted with DCM. Extracts were dried over Na₂SO₄, filtered, and concentrated to give an oil (0.276 g) after chromatography (100:1→20:1, DCM:MeOH w/1.0% conc. $NH_{3(aq)}$); MS: m/z 540 (M+); ¹H NMR (CDCl₃) δ 8.27 (s), 7.83 (d), 7.68–7.30 (m), 7.01 (d), 6.82 (d), 6.54 (dd), 4.35–4.12 (m), 3.84 (s), 3.82 (s), 3.50–3.28 (m), 3.19–2.93 (m), 2.80–2.65 (m), 2.01 (s), 1.78 (t), 1.36 (t).

Example 50

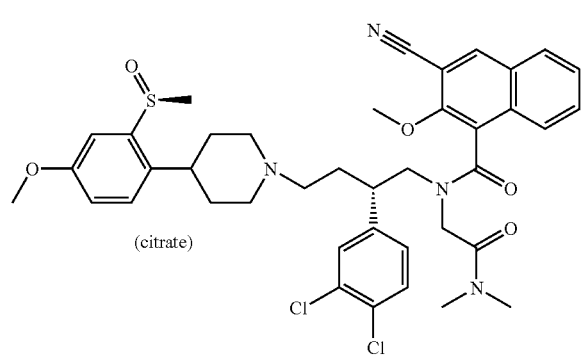

(citrate)

N-[(S)-2-(3,4-dichlorophenyl)-4-[4-[4-methoxy-
(S*)-2-methylsulfinyl)phenyl]-1-piperidinyl]butyl]-
N-[2-oxo-2-dimethylaminoethyl]-3-cyano-2-
methoxy-1-naphthamide citrate To a solution of N-[(S)-2-(3,4-dichlorophenyl)-4-[4-[4-methoxy-(S*)-2-(methylsulfinyl)-phenyl]-1-piperidinyl]butyl]-N-[2-hydroxy-2-oxoethyl]-3-cyano-2-methoxy-1-naphthamide citrate, N,N-diisopropylethylamine, and dry DCM was added tetramethylfluoroformamidinium hexafluorophosphate (5 equiv.). After 5 min, dimethylamine (2M in THF) (150 equiv.) was then added. After stirring overnight, the mixture was concentrated, and the residue was purified by flash chromatography. The purified free base (45%) was converted to the citrate salt and isolated by filtration from Et$_2$O. MS APCI, m/z=763 (M$^+$) (free base); HPLC$^b$ 16.5.

Example 51

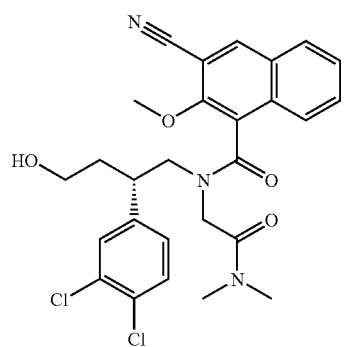

N-[2-(S)-(3,4-dichlorophenyl)-4-hydroxybutyl]-N-
[2-oxo-2-dimethylaminoethyl]-3-cyano-2-methoxy-
1-naphthamide N-[2-(S)-(3,4-dichlorophenyl)-4-(tert.-butyl-dimethylsilyloxy)-butyl]-3-cyano-2-methoxy-1-naphthamide$^a$ and sodium hydride (1.3 equiv.) in dry DMF was stirred for 2 h, cooled (ice bath), then treated with N,N-dimethyl bromoacetamide (1.4 equiv.). Following deprotection (1M tetrabutylammoniun fluoride in THF), the required product (85%) was obtained as a mixture of atropisomers. MS APCI, m/z=528 (M$^+$). HPLC$^b$ 17.6.

$^a$Prepared from N-[2-(S)-(3,4-dichlorophenyl)-4-hydroxybutyl]-3-cyano-2-methoxy-1-naphthamide and tert. butyl dimethylsilyl chloride.
$^b$Analytical HPLC conditions employed were the following: Hewlett Packard HP1050 system using a Zorbax RX-C8, 4.6×250 mm, 5 micron column at 30° C., with the following gradient: 0–0.5 min; 10% Solvent B, then ramping linearly to 100% Solvent B at 30 min at a fixed flow rate of 1.2 mL/min (Solvent A: 0.1% TFA in water; Solvent B: 0.1% TFA in acetonitrile); UV detection at 215 and 260 nm; retention time given in min.

What is claimed is:

1. A compound having the formula

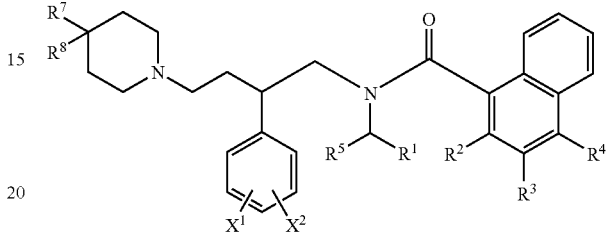

wherein:

$R^1$ is $C_{1-4}$alkyl, substituted by 1 or 2 substituents selected from —NR$^a$R$^a$, —NR$^a$C(=O)R$^a$, —C(=O)NR$^a$R$^a$, —OR$^a$, —OC(=O)R$^a$, —C(=O)OR$^a$, —S(=O)$_n$ $C_{1-6}$alkyl, nitro, cyano and $C_{1-3}$haloalkyl; phenyl substituted by 0, 1, 2 or 3 substituents selected from —NR$^a$R$^a$, —NR$^a$C(=O)R$^a$, —C(=O)NR$^a$R$^a$, —OR$^a$, —OC(=O)R$^a$, —C(=O)OR$^a$, —S(=O)$_n$$C_{1-6}$alkyl, nitro, cyano and $C_{1-3}$haloalkyl; or a 5- or 6-membered ring heterocycle containing 1, 2 or 3 heteroatoms each independently selected from O, N and S and additionally having 0 or 1 oxo groups and 0 or 1 fused benzo rings;

$R^2$ is H, halogen, —OR$^9$ or $C_{1-4}$alkyl;

$R^3$ is H, halogen, —OR$^9$ or —CN;

$R^4$ is H, halogen, —OR$^9$ or $C_{1-4}$alkyl;

$R^5$ is H or CH$_3$;

$R^7$ is phenyl substituted by 0, 1, 2 or 3 substituents selected from $C_{1-6}$alkyl, —NR$^a$R$^a$, —NR$^a$C(=O)R$^a$, —C(=O)NR$^a$R$^a$, —OR$^a$, —OC(=O)R$^a$, —C(=O) R$^a$, —C(=O)OR$^a$, —S(=O)$_n$$C_{1-6}$alkyl, nitro, cyano, $C_{1-3}$haloalkyl, trifluoromethylthio, trifluoromethylsulfinyl, $C_{1-6}$alkanesulfonamido, succinamido, carbamoyl, $C_{1-6}$alkylcarbamoyl, di-$C_{1-6}$alkylcarbamoyl, $C_{1-6}$alkoxy-$C_{1-6}$alkylcarbamoyl, ureido, $C_{1-6}$alkylureido, di($C_{1-6}$alkyl)ureido, bromo, fluoro, chloro and dimethylcarbamoylmethylureido; or $R^7$ is a 5- or 6-membered ring heterocycle containing 1, 2 or 3 heteroatoms each independently selected from O, N and S, said heterocycle additionally having 0 or 1 oxo groups and being substituted by 0 or 1 substituents selected from —OR$^a$, —OC(=O)R$^a$, —C(=O)OR$^a$, —C(=O)R$^a$, —NR$^a$R$^a$, —NR$^a$C(=O)R$^a$ and —C(=O)NR$^a$R$^a$; or $R^7$ is hydrogen or NR$^a$R$^a$;

$R^8$ is selected from hydrogen, —OR$^a$, —OC(=O)R$^a$, —C(=O)OR$^a$, —C(=O)R$^a$, —NR$^a$R$^a$, —NR$^a$C(=O) R$^a$, —C(=O)NR$^a$R$^a$, $C_{1-6}$alkyl, carbamoyl, $C_{1-6}$alkylcarbamoyl, and bis($C_{1-6}$alkyl)carbamoyl;

$R^a$ is independently at each instance hydrogen or $C_{1-6}$alkyl;

$R^9$ is $C_{1-6}$alkyl, phenyl or phenyl$C_{1-6}$alkyl;

n is 0, 1 or 2; and $X^1$ and $X^2$ are independently H, —$CH_3$ or halogen; or any pharmaceutically-acceptable salt thereof.

2. A compound according to claim 1, wherein $X^1$ and $X^2$ are H or halogen, and at least one of $X^1$ and $X^2$ are halogen.

3. A compound according to claim 1, wherein $R^1$ is $C_{1-4}$alkyl, substituted by 1 or 2 substituents selected from —C(=O)NR$^a$R$^a$, —C(=O)OR$^a$ and $C_{1-3}$haloalkyl; phenyl substituted by 0, 1, 2 or 3 substituents selected from —NR$^a$R$^a$, —NR$^a$C(=O)R$^a$, —OR$^a$, —OC(=O)R$^a$, nitro, cyano and $C_{1-3}$haloalkyl; or a 5- or 6-membered ring heterocycle containing 1, 2 or 3 nitrogen atoms.

4. A compound according to claim 1, wherein $R^1$ is $C_{1-4}$alkyl, substituted by 1 or 2 substituents selected from —C(=O)NR$^a$R$^a$, —C(=O)OR$^a$ and $C_{1-3}$haloalkyl; phenyl substituted by 0, 1, 2 or 3 substituents selected from —NR$^a$R$^a$, —NR$^a$C(=O)R$^a$, —OR$^a$, —OC(=O)R$^a$, nitro, cyano and $C_{1-3}$haloalkyl; or a 5- or 6-membered ring heterocycle containing 1, 2 or 3 nitrogen atoms.

5. A compound according to claim 4, wherein:

$R^7$ is phenyl substituted by 0, 1, 2 or 3 substituents selected from $C_{1-6}$alkyl, —NR$^a$R$^a$, —NR$^a$C(=O)R$^a$, —C(=O)NR$^a$R$^a$, —OR$^a$, —OC(=O)R$^a$, —C(=O)R$^a$, —C(O)OR$^a$, —S(=O)$_n$C$_{1-6}$alkyl, nitro, cyano, $C_{1-3}$haloalkyl, bromo, fluoro and chloro.

6. A compound according to claim 4, wherein:

$R^7$ is a 5- or 6-membered ring heterocycle containing 1 or 2 heteroatoms each independently selected from O, N and S and additionally having 0 or 1 oxo groups and being substituted by 0 or 1 —C(=O)NR$^a$R$^a$.

7. A compound according to claim 4, wherein $R^7$ is NR$^a$R$^a$.

8. A compound according to claim 5, wherein $R^8$ is selected from hydrogen, —NR$^a$R$^a$, —NR$^a$C(=O)R$^a$ and —C(=O)NR$^a$R$^a$.

9. A compound according to claim 6, wherein $R^8$ is selected from hydrogen, —NR$^a$R$^a$, —NR$^a$C(=O)R$^a$ and —C(=O)NR$^a$R$^a$.

10. A compound according to claim 7, wherein $R^8$ is selected from hydrogen, —NR$^a$R$^a$, —NR$^a$C(=O)R$^a$ and —C(=O)NR$^a$R$^a$.

* * * * *